US006831099B1

(12) United States Patent
Crews et al.

(10) Patent No.: US 6,831,099 B1
(45) Date of Patent: Dec. 14, 2004

(54) ENZYME INHIBITION

(75) Inventors: Craig M. Crews, New Haven, CT (US); Mikael Elofsson, Umea (SE); Ute Splittgerber, La Mesa, CA (US); Ny Sin, East Hampton, CT (US); Kyung Bo Kim, Hamden, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/569,748

(22) Filed: May 11, 2000

Related U.S. Application Data

(60) Provisional application No. 60/133,847, filed on May 12, 1999.

(51) Int. Cl.[7] .............................................. A01N 43/20

(52) U.S. Cl. ...................... 514/475; 514/539; 514/588; 514/209; 514/541; 514/546; 514/520; 514/461; 514/2; 514/18; 514/21; 530/350

(58) Field of Search ............................ 530/350; 514/2, 514/18, 21, 588, 539, 475, 209, 541, 546, 520, 461

(56) References Cited

U.S. PATENT DOCUMENTS

| | | | | |
|---|---|---|---|---|
| 4,990,448 A | * | 2/1991 | Konishi et al. | 435/106 |
| 5,071,957 A | * | 12/1991 | Konishi et al. | 530/330 |
| 5,340,736 A | | 8/1994 | Goldberg | 435/226 |
| 5,723,492 A | * | 3/1998 | Chandrakumar et al. | 514/539 |
| 5,756,764 A | | 5/1998 | Fenteany et al. | 548/541 |
| 6,150,415 A | * | 11/2000 | Hammock et al. | 514/588 |

FOREIGN PATENT DOCUMENTS

| | | |
|---|---|---|
| EP | 411660 A1 | 6/1991 |
| WO | 411666 * | 6/1991 |

OTHER PUBLICATIONS

The Journal of Antibiotics, vol. 45, No. 11, pp. 1746–1752, Nov. 1992.*

Spaltenstein et al., "Design and Synthesis of Novel protease Inhibitors. Tripeptide . . . Nanomolar Inactivators of the Proteasome", Tetrahedron Letter, vol. 37, No. 9, pp. 1343–1346, 1996.

Hoshi et al., "A Total Synthesis of . . . Determination . . . Epoxide Ring", Tetrahedron Letters, vol. 34, No. 6, pp. 1047–1050, 1993.

Bogyo et al., "Substrate binding . . . proteasome . . . affinity probes", Chemistry & Biology, vol. 5, No. 6, pp 307–320, Jun. 1998.

Bogyo et al., "Covalent modification . . . of proteasomal . . . HsIV by a new class of inhibitors", Proc. Natl. Acad. Sci. USA, vol. 94, pp. 6629–6634, Jun. 1997.

Groll et al., "Crystal Structure of Epoxomicin . . . Selectivity of . . . Protease Inhibitors", J. Am. Chem. Soc. 2000, 122, pp 1237–1238.

Kim et al., "Proteasome Inhibition . . . Dihydroeponemycin . . . Into Specificity and Protency", Bioorganic & Medicinal Chemistry Letters 9 (1999) pp 3335–3340.

Sin et al., "Total Sytnhesis of the Potent Proteasome . . . Epoxomicin . . . Understanding Proteasome Biology", Biorgainc & Medicinal Chemistry Letters 9 (1999) pp 2283–2288.

Elofsson et al., "Towards subunit–specific proteasome inhibitors: . . . of peptide α',β'–epoxyketones", Chemistry & Biology, Research Paper, 1999, vol. 6, No. 11, pp 811–822.

Meng et al., "Epoxomicin, a potent and selective . . . anti–inflammatory activity", Proc. Natl. Acad. Sci. USA, vol. 96, pp. 10403–10408, Medical Sciences, Aug. 1999.

Meng et al., "Eponemycin Exerts Its Antitumor Effect Through The Inhibition of Proteasome Function", Cancer Research, vol. 59, No. 12, pp 2798–2801, Jun. 15, 1999.

Schwarz et al., "The Selective Proteasome Inhibitors Lactacystin . . . Used To Either Up– or Down–Regulate Antigen . . . at Nontoxic Doses[1] ", Journal of Immunology, vol. 164(12), pp 6147–57, Jun. 15, 2000.

Groettrup and Schmidtke, "Selective proteasome inhibitors: modulators of antigen presentation?", Drug Discovery Today, vol. 4(2), pp 63–71, Feb. 1999.

Hanada et al., "Epoxomicin, A New Antitumor Agent of Microbial Origin", The Journal of Antibiotics, vol. 45, No. 11, Nov. 1992, pp 1746–1752.

Meng et al., "Eponemycin Exerts Its Antitumor Effect through the Inhibition of Proteasome Function", Cancer Research 29, 2798–2801, Jun. 15, 1999.

Figueiredo–Pereira et al., "The Antitumor Drug Aclacinomycin A. Which Inhibits the Degradation of Ubiquitinated Proteins, Shows Selectivity for the Chymotrypsin–like Activity of the Bovine Pituitary 20 S Proteasome", The Journal of Biological Chemistry, vol. 271, No. 28, Issue of Jul. 12, pp 16455–16459, 1996.

Adams et al., "Proteasome Inhibitors: A Novel Class of Potent and Effective Antitumor Agents", Cancer Research 59, 2615–2622, Jun. 1, 1999.

(List continued on next page.)

Primary Examiner—Karen Cochrane Carlson
Assistant Examiner—Hope A. Robinson
(74) Attorney, Agent, or Firm—Ropes & Gray LLP

(57) ABSTRACT

Peptide-based compounds including heteroatom-containing, three-membered rings efficiently and selectively inhibit specific activities of N-terminal nucleophile (Ntn) hydrolases. The activities of those Ntn having multiple activities can be differentially inhibited by the compounds described. For example, the chymotrypsin-like and PGPH activities of the 20S proteasome can be selectively inhibited with the inventive compounds. The peptide-based compounds include an electron withdrawing group adjacent to the ring functionality, and the peptide include at least three peptide units. Among other therapeutic utilities, the peptide-based compounds exhibit anti-inflammatory and inhibition of cell proliferation, involving therapeutic applications for these compounds.

21 Claims, 6 Drawing Sheets

OTHER PUBLICATIONS

Favit et al., "Prevention of β–Amyloid Neurotoxicity by Blockade of the Ubiquitin–Proteasome Protealytic Pathway", Journal of Neurochemistry, vol. 75, No. 3, 2000, pp 1258–1263.

Schwarz et al., "The Selective Proteasome Inhibitors Lactacystin and Epoxomicin Can Be Used to Either Up– or Down–Regulate Antigen Presentation at Nontoxic Doses[1]", The Journal of Immunology, pp 6148–6157.

* cited by examiner

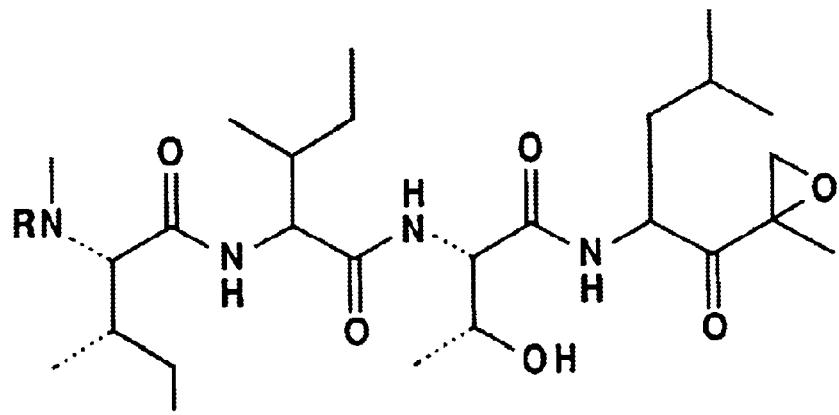
Epoxomicin: R=Acetyl
Epoxomicin-biotin: R=
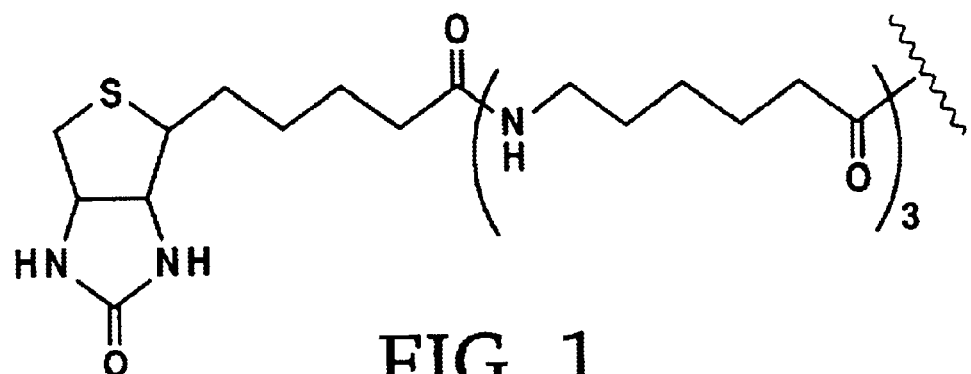
FIG. 1
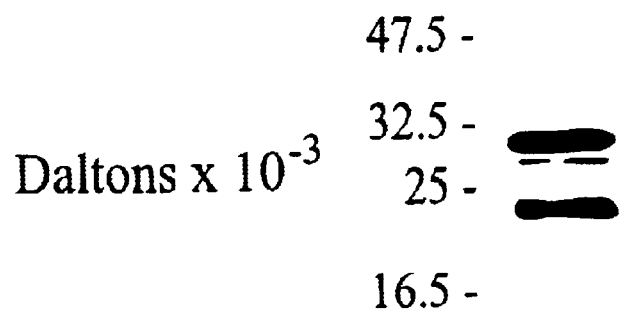
FIG. 2

ENZYME INHIBITION

This application claims the benefit of Provisional application Ser. No. 60/133,847, filed on May 12, 1999.

This invention was made with support from the Government, pursuant to a grant from the National Institutes of Health, Grant CA74967-01. The Government has certain rights in this invention.

TECHNICAL FIELD

This invention relates to compounds and methods for enzyme inhibition. In particular, the invention relates to therapeutic methods deriving from enzyme inhibition.

BACKGROUND

In eukaryotes, protein degradation is predominately mediated through the ubiquitin pathway in which proteins targeted for destruction are ligated to the 76 amino acid polypeptide ubiquitin. Once targeted, ubiquitinated proteins then serve as substrates for the 26S proteasome, a multicatalytic protease, which cleaves proteins into short peptides through the action of its three major proteolytic activities. While having a general function in intracellular protein turnover, proteasome-mediated degradation also plays a key role in many processes such as major histocompatibility complex (MHC) class I presentation, apoptosis, cell division, and NF-κB activation.

The 20S proteasome is a 700 kDa cylindrical-shaped multicatalytic protease complex comprised of 28 subunits organized into four rings. In yeast and other eukaryotes, 7 different α subunits form the outer rings and 7 different β subunits comprise the inner rings. The α subunits serve as binding sites for the 19S (PA700) and 11S (PA28) regulatory complexes, as well as a physical barrier for the inner proteolytic chamber formed by the two β subunit rings. Thus, in vivo, the proteasome is believed to exist as a 26S particle ("the 26S proteasome"). In vivo experiments have shown that inhibition of the 20S form of the proteasome can be readily correlated to inhibition of 26S proteasome. Cleavage of amino-terminal prosequences of β subunits during particle formation expose amino-terminal threonine residues, which serve as the catalytic nucleophiles. The subunits responsible for catalytic activity in proteaseome thus possess an amino terminal nucleophilic residue, and these subunits belong to the family of N-terminal nucleophile (Ntn) hydrolases (where the nucleophilic N-terminal residue is, for example, Cys, Ser, Thr, and other nucleophilic moieties). This family includes, for example, penicillin G acylase (PGA), penicillin V acylase (PVA), glutamine PRPP amidotransferase (GAT), and bacterial glycosylasparaginase. In addition to the ubiquitously expressed β subunits, higher vertebrates also possess three γ-interferon-inducible β subunits (LMP7, LMP2 and MECL1), which replace their normal counterparts, X, Y and Z respectively, thus altering the catalytic activities of the proteasome. Through the use of different peptide substrates, three major proteolytic activities have been defined for the eukaryote 20S proteasome: chymotrypsin-like activity (CT-L), which cleaves after large hydrophobic residues; trypsin-like activity (T-L), which cleaves after basic residues; and peptidylglutamyl peptide hydrolyzing activity (PGPH), which cleaves after acidic residues. Two additional less characterized activities have also been ascribed to the proteasome: BrAAP activity, which cleaves after branched-chain amino acids; and SNAAP activity, which cleaves after small neutral amino acids. The major proteasome proteolytic activities appear to be contributed by different catalytic sites, since inhibitors, point mutations in β subunits and the exchange of γ interferon-inducing β subunits alter these activities to various degrees.

The 20S proteasome plays important roles in cell growth regulation, major histocompatibility complex class I presentation, apoptosis, antigen processing, NF-κB activation, and transduction of pro-inflammatory signals.

Small molecules which have been used to inhibit proteasome activity include lactacystin, and short peptides including aldehyde, vinyl sulfone, boronic acid and glyoxal functional groups. These compounds generally lack the specificity, stability, or potency necessary to explore the roles of the proteasome at the cellular and molecular level. For example, peptide aldehydes also inhibit lysosomal and $Ca^{+2}$-activated proteases, thus complicating a precise dissection of their effects on cells. Vinyl sulfone-based inhibitors have been reported to bind and inhibit intracellular cysteine proteases (for example, cathepsin S), in addition to their actions against the proteasome. Lactacystin has a rate of proteasome inactivation which is significantly slower than that of vinyl sulfone peptide inhibitors. Lactacystin is also non-specific for 20S proteasome, as it has been found to significantly decrease the hydrolysis rate of human platelet lysosomal cathepsin A-like enzyme at pH 5.5.

SUMMARY

Enzyme inhibitors are valuable tools that enable the elucidation of details in cellular events that are regulated by these enzymes. Additionally, enzyme inhibitors have therapeutic applications and can be used to carry out mechanistic studies of the machinery of enzymatic processes. The invention relates to the discovery that classes of molecules known as peptide α',β'-epoxides and peptide α',β'-aziridines can bind efficiently, irreversibly and selectively to N-terminal nucleophile (Ntn) hydrolases, and can specifically inhibit particular activities of enzymes having multiple catalytic activity.

Once thought merely to dispose of denatured and misfolded proteins, the proteasome is now recognized as constituting proteolytic machinery that regulates the levels of diverse intracellular proteins through their degradation in a signal-dependent manner. Hence, there is great interest in identifying reagents that can specifically perturb the activities of the proteasome and other Ntn hydrolases and thereby be used as probes to study the role of these enzymes in biological processes. Compounds that target the Ntn hydrolases are herein described, synthesized and investigated. Peptide epoxides and peptide aziridines that can potently, selectively, and irreversibly inhibit particular proteasome activities are disclosed and claimed.

Particular peptide epoxides and peptide aziridines modify three catalytic subunits of the 20S proteasome resulting in inhibition primarily of the chymotrypsin-like activity; the trypsin-like and PGPH activities were also inhibited at approximately 100-fold and 1000-fold slower rates, respectively. Furthermore, in comparison with other potent irreversible proteasome inhibitors, peptide epoxides and peptide aziridines inhibit the chymotrypsin-like activity at least about 80-fold faster than lactacystin and at least about four-fold faster than clasto-lactacystin β-lactone. Even higher rates are obtainable.

Other particular peptide epoxides and peptide aziridines primarily inhibit PGPH activity, while having far less inhibitory effect on chymotrypsin-like activity, and virtually no effect on trypsin-like activity. In contrast to the enzyme inhibitors described above, which are highly specific for chymotrypsin-like activity of the proteasome, these other particular PGPH-specific peptide epoxides and peptide aziridines inhibit a catalytic step which is believe to be a rate-limiting step in protein degradation. Their use in elucidating the role(s) of other proteasomal subunits is thus limited. The PGPH-specific inhibitors allow separation of contributions of this particular catalytic activity in biological processes mediated by the proteasome.

Unlike several other peptide-based inhibitors, the peptide epoxides and peptide aziridines described herein do not substantially inhibit non-proteasomal proteases such trypsin, chymonypsin, cathepsin B, papain, and calpain at concentrations up to 50 $\mu$M. At higher concentrations, inhibition is observed, but is competitive and not irreversible, since the inhibitor merely competes with the substrate. The novel peptide epoxides and peptide aziridines are also shown to inhibit NF-κB activation and to stabilize p53 levels in cell culture. Moreover, we have demonstrated the potent anti-inflammatory activity of peptide epoxides and peptide aziridines in a mouse model of cutaneous inflammation. Thus, these compounds can be unique molecular probes, which have the versatility to explore Ntn enzyme function in normal biological and pathological processes.

In one aspect, the invention provides N-terminal nucleophile hydrolase inhibitors comprising a heteroatom-containing, three-membered ring, where the ring is bonded to an electron-withdrawing group, and the electron-withdrawing group is bonded to a peptide moiety. These inhibitors can inhibit catalytic activity of N-terminal nucleophile hydrolase enzymes (for example, the 20S proteasome, or the 26S proteasome) when said inhibitor is present at concentrations below about 50 $\mu$M, and do not inhibit catalytic activity of non-proteasomal proteases when the inhibitor is present at concentrations below about 50 $\mu$M. Regarding the 20S proteasome, particular hydrolase inhibitors inhibit chymotrypsin-like activity of the 20S proteasome when the inhibitor is present at concentrations below about 5 $\mu$M, and does not inhibit trypsin-like activity or PGPH activity of the 20S proteasome when is present at concentrations below about 5 $\mu$M. Other particular hydrolase inhibitors inhibit PGPH activity of the 20S proteasome when the inhibitor is present at concentrations below about 50 $\mu$M, and does not inhibit chymotrypsin-like or trypsin-like activity of the 20S proteasome when the inhibitor is present at concentrations below about 50 $\mu$M. The hydrolase inhibitor can be, for example, a peptide $\alpha',\beta'$-epoxy ketone or $\alpha',\beta'$-aziridine ketone, and the peptide can be a tetrapeptide. The tetrapeptide can include branched or unbranched side chains such as hydrogen, $C_{1-6}$ alkyl, $C_{1-6}$ hydroxy alkyl, $C_{1-6}$ alkoxy alkyl, aryl, and aryl-substituted $C_{1-6}$ alkyl, $C_{1-6}$ amide, $C_{1-6}$ amine, $C_{1-6}$ carboxylic acid, $C_{1-6}$ carboxyl ester, $C_{1-6}$ thiol, or $C_{1-6}$ thioether, for example isobutyl, 1-naphthyl, phenylmethyl, and 2-phenylethyl. The $\alpha'$-carbon of the $\alpha',\beta'$-epoxy ketone or $\alpha',\beta'$-aziridine ketone can be a chiral carbon atom, such as an (R) or β configured carbon, as these are defined herein.

In another aspect, the invention includes a method of making a peptide $\alpha',\beta'$-epoxy ketone or $\alpha',\beta'$-aziridine ketone. The method involves synthesizing a first molecule by providing a tripeptide; acetylating the amino terminal of the tripeptide to make an acetylated tripeptide; and catalytically hydrogenating the acetylated tripeptide to make the first molecule. The method further involves synthesizing a second molecule by alkenylating a Weinreb amide of an amino acid having an amino terminal protection group to form an $\alpha',\beta'$-unsaturated ketone; forming a three-membered, heteroatom-containing ring at the $\alpha',\beta'$-unsaturation side to form an $\alpha',\beta'$-epoxy ketone or an $\alpha',\beta'$-aziridine ketone; removing the amino terminal protection group to form the second molecule. The method also involves coupling the first and second molecules to make a peptide $\alpha',\beta'$-epoxy ketone or $\alpha',\beta'$-aziridine ketone. If the tripeptide has hydroxy side chains, protecting the hydroxy side chain to make a protected hydroxy side chain-containing tripeptide; and deprotecting the hydroxy side chain after said coupling are also desirable.

In another aspect, the invention provides pharmaceutical compositions, including a pharmaceutically acceptable carrier, and a pharmaceutically effective amount of the hydrolase inhibitor, which ameliorates the affects of Alzheimer's disease, muscle-wasting diseases, cancer, chronic infectious diseases, fever, muscle disuse, denervation, nerve injury, and wasting, among others;

In another aspect, the invention provides anti-inflammatory compositions.

In another aspect, the invention provides methods for the following: inhibiting or reducing HIV infection in a subject; affecting the level of viral gene expression in a subject; altering the variety of antigenic peptides produced by the proteasome in an organism; determining whether a cellular, developmental, or physiological process or output in an organism is regulated by the proteolytic activity of a particular Ntn hydrolase; treating Alzheimer's disease in a subject; reducing the rate of muscle protein degradation in a cell; reducing the rate of intracellular protein degradation in a cell; reducing the rate of p53 protein in a cell; inhibiting the growth of p53-related cancers in a subject; inhibiting antigen presentation in a cell; suppressing the immune system of a subject; inhibiting IκB-α degradation in an organism; reducing the content of NF-κB in a cell, muscle, organ or subject; affecting cyclin-dependent eukaryotic cell cycles; treating proliferative disease in a subject; affecting proteasome-dependent regulation of oncoproteins in a cell; treating cancer growth in a subject; treating p53-related apoptosis in a subject; and screening proteins processed by N-terminal nucleophile hydrolases in a cell. Each of these methods involves administering or contacting an effective amount of a composition comprising the hydrolase inhibitors disclosed herein, to a subject, a cell, a tissue, an organ or an organism.

In a further aspect, the invention provides a method of making an α,β-aziridine ketone, the method including reacting an α-halo ketone with a) a boron-containing reagent, and with b) an imine for a time and under conditions sufficient to form an α,β-aziridine ketone.

As used herein, the term "inhibitor" is meant to describe a compound that blocks or reduces an activity of an enzyme (for example, inhibition of proteolytic cleavage of standard fluorogenic peptide substrates such as suc-LLVY-AMC (SEQ ID NO:1), Box-LLR-AMC and Z-LLE-AMC, inhibition of various catalytic activities of the 20S proteasome). An inhibitor can act with competitive, uncompetitive, or noncompetitive inhibition. An inhibitor can bind reversibly or irreversibly, and therefore the term includes compounds that are suicide substrates of an enzyme. An inhibitor can modify one or more sites on or near the active site of the enzyme, or it can cause a conformational change elsewhere on the enzyme.

As used herein, "enzyme" can be any partially or wholly proteinaceous molecule which carries out a chemical reaction in a catalytic manner. Such enzymes can be native enzymes, fusion enzymes, proenzymes, apoenzymes, denatured enzymes, farnesylated enzymes, ubiquitinated enzymes, fatty acylated enzymes, gerangeranylated enzymes, GPI-linked enzymes, lipid-linked enzymes, prenylated enzymes, naturally-occurring or artificially-generated mutant enzymes, enzymes with side chain or backbone modifications, enzymes having leader sequences, and enzymes complexed with non-proteinaceous material, such as proteoglycans, proteoliposomes. Enzymes can be made by any means, including natural expression, promoted expression, cloning, various solution-based and solid-based peptide syntheses, and similar methods known to those of skill in the art.

As used herein, the term "peptide" includes not only standard amide linkage with standard α-substituents, but commonly utilized peptidomimics, other modified linkages, non-naturally occurring side chains, and side chain modifications, as detailed below.

As used herein, the term "heteroatom-containing, three-membered ring" includes moieties with two carbon atoms and a single heteroatom, such as oxygen or nitrogen.

As used herein, the term "treating" includes reversing, reducing, or arresting the symptoms, clinical signs, and underlying pathology of a condition in manner to improve or stabilize a subject's condition.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 1 is a generalized molecular structure of epoxomicin and epoxomicin-biotin.

FIG. 2 is a photocopy of an electrophoretic gel showing a) separation of bovine brain proteasome catalytic subunits without (lane 1) and with (lane 2) 50 μM epoxomicin pretreatment, and b) human B cell lymphoma cells LCL 721.45 (lane 3) and LCL 721.174 (lane 4), both labeled with 5 μM epoxomicin-biotin.

DETAILED DESCRIPTION

Figure 3:
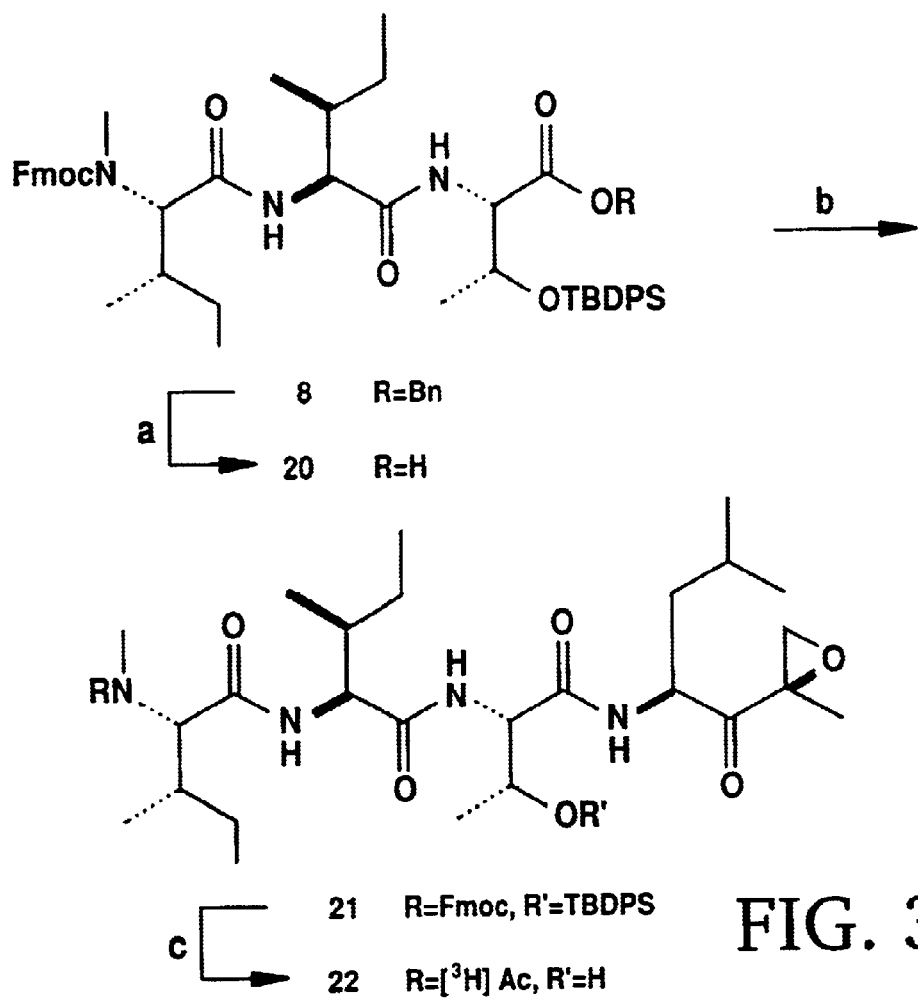
FIG. 3 is a reaction scheme of the synthesis of [$^3$H]-epoxomicin.

The invention involves compounds useful as enzyme inhibitors. These compounds include peptide and epoxide or aziridine moieties. These compounds are generally useful as inhibitors of enzymes having a nucleophilic group at the N-terminus. For example, activities of enzymes or enzyme subunits having N-terminal amino acids with nucleophiles in their side chains, such as threonine, serine, or cysteine can be successfully inhibited by the enzyme inhibitors described herein. For example, activities of enzymes or enzyme subunits having non-amino acid nucleophilic groups at their N-termini, such as for example, protecting groups or carbohydrates, can also be successfully inhibited by the enzyme inhibitors described herein.

While not bound by any particular theory of operation, it is believed that such N-terminal nucleophiles of Ntn are able to form covalent adducts with the epoxide or aziridine functional group of the enzyme inhibitors described herein. For example, in the β5/Pre2 subunit of 20S proteasome, the N-terminal threonine is believed to irreversibly form a morpholino or piperazino adduct upon reaction with a peptide epoxide or peptide aziridine, respectively, such as those described below. Such adduct formation would involve a ring-opening reaction of the heteroatom-containing, three-membered ring.

The epoxide- or aziridine-containing compounds preferably contain groups proximate the heteroatom-containing, three-membered rings, such that a ring-opening reaction of the heteroatom-containing three-membered ring is facilitated. Such groups include electron-withdrawing groups (E.W.G.) adjacent to (for example, at a carbon vicinal to a carbon atom of the three-membered, heteroatom-containing ring), or in electronic communication with (for example, via a carbon atom, or an alkenyl or alkynyl linkage), epoxide or aziridine functionalities. The E.W.G. can be bonded to one of the carbon atoms of the heteroatom-containing, three-membered ring. E.W.G. include, for example, cyano, isocyano, nitro, amide, sulfonyl, β-carboxy vinyl, sulfinyl, β,β-dicyano vinyl, formyl, carboxyl, alkyloxy- and aryloxy-carbonyl, 1-tetrazolyl, carbamoyl, sulfamoyl, carbonyl, sulfoxide groups, and halogenated or dihalogenated carbon atoms such as —CHX—, —CXX'—, —CRX— (where X and X' are independently selected halogens, and R is a carbon-containing substituent such as alkyl, aryl alkenyl, alkynyl and the like). In some preferred embodiments, E.W.G. is a carbonyl group.

In some embodiments, it may be desirable to utilize E.W.G. that are of size, charge, and polarity sufficient to interact electronically with particular polar or charged moieties within an Ntn hydrolase. For example, an ionized aspartate or glutamate side chain can be present in the Ntn, and interact with, and stabilize, an electron-withdrawing group present in a peptide epoxide. Such groups act as an "anion hole," with which E.W.G. can interact when enzyme inhibitors are bound to Ntn, resulting in increased electrophilicity of E.W.G.

Some peptide epoxide or peptide aziridine compounds have ketone functionality as the electron-withdrawing group, along with epoxide or aziridine functional groups.

Particular examples are peptide α',β'-epoxy ketones or peptide α',β'-aziridine ketones, in which the carbon atoms forming two of the three members of the epoxide or aziridine ring are one (α') and two (β') carbons from the ketone, and the ketone carbon is bonded to one of the carbon atoms of the heteroatom-containing, three-membered ring. Further groups can be bonded to α' or β' carbons such as hydrogen, branched or unbranched $C_{1-4}$ alkyl groups, including methyl, ethyl, propyl and butyl groups. Groups bonded to α' or β' carbons can be further substituted with hydroxy, halogen, amino, carboxy, carbonyl, thio, sulfide, ester, amide or ether functionality.

For example, a carboxylic acid group can be bonded directly to the α' carbon, or via a linker. The linker can be $C_{1-4}$ alkylene, $C_{2-5}$ alkenylene, $C_{2-5}$ alkynylene, aryl, oxygen, sulfur, amine. This carboxylic acid can be part of a peptide moiety extending from the α' carbon of the heteroatom-containing, three-membered ring. In this way, peptides containing side chains can be constructed. Such side chains can be labeled as P1', P2', and so forth, with P1' being the first side chain adjacent to the α' carbon, P2' being the second, and so forth. Optimization of side chains for P1', P2' and other positions can result in enzyme inhibitors with desirable specificity, or desirable inhibition rates. Side chains for P1', P2' and so forth can be any of those side chains discussed herein.

In embodiments including such groups bonded to α' carbons, the stereochemistry of the α'-carbon (that carbon forming a part of the epoxide or aziridine ring) can be (R) or (S). The invention is based, in part, on the structure-function information disclosed herein, which suggests the following preferred stereochemical relationships. Note that a preferred compound may have a number of stereocenters having the indicated up-down (or β-α, where β as drawn herein is above the plane of the page) or (R)-(S) relationship (that is, it is not required that every stereocenter in the compound conform to the preferences stated). In some preferred embodiments, the stereochemistry of the α' carbon is (R), that is, the X atom is β, or above the plane of the molecule, when drawn as below. For example, the following general structural formula I demonstrates a preferred stereochemistry for some embodiments:

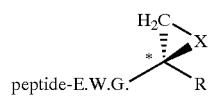

I where X is oxygen or an NH or N-alkyl group, E.W.G. is an electron withdrawing group as described above, "peptide" is a peptide as describe below, and R is a hydrogen atom, a branched or unbranched $C_{1-4}$ alkyl group, which can be further substituted with hydroxy, halogen, amino, carboxy, carbonyl, thio, sulfide, ester, amide or ether functionality. For some embodiments, the X atom should be configured as above in order to facilitate interaction with an N-terminal nucleophilic group in an Ntn hydrolase. For example, irreversible interactions of enzyme inhibitors with the β5/Pre2 subunit of 20S proteasome which lead to inhibition appear to be facilitated by the configuration illustrated above. In the case of other Ntn hydrolases, the opposite stereochemistry of the α-carbon of the peptide epoxides or peptide aziridines may be preferred.

In the case illustrated above, the β' carbon is substituted with two hydrogen atoms. Regarding the stereochemistry, the chiral α' carbon is indicated with a star, and the Cahn-Ingold-Prelog rules for determining absolute stereochemistry are followed. These rules are described, for example, in *Organic Chemistry*, Fox and Whitesell; Jones and Bartlett Publishers, Boston, Mass. (1994); Section 5–6, pp 177–178, which section is hereby incorporated by reference. The stereochemistry of the α' carbon is (R) when the oxygen or nitrogen has the highest priority, the peptide-E.W.G. group has second highest priority, and the —CH$_2$—X— group has third highest priority. If the relative priorities of the peptide-E.W.G., —CH$_2$—X—, and R groups change, the nominal stereochemistry can change, but the essential configuration of the groups can remain the same, for some preferred embodiments. That is, referring to the general structure immediately above, peptide-E.W.G. is joined to the chiral α' carbon from the left, R is joined to the chiral α' carbon from the right, and the X atom(s) project(s) from the plane of the page. The nitrogen atom of an aziridine ring can also, in principle, be chiral, as discussed in March, *Advanced Organic Chemistry*, 4$^{th}$ Ed. (1992) Wiley-Interscience, New York, pp. 98–100, which pages are incorporated herein by reference.

The peptide epoxides or peptide aziridines also include a peptide moiety. The peptide moiety is bonded to the electron-withdrawing group. The bond is made between the electron-withdrawing group and any portion of the peptide. For example, in some preferred embodiments, the E.W.G. is bonded to the terminal backbone unit, such as for example, to the carboxy terminus of the peptide. Alternatively, the E.W.G. can be bonded to the amino terminus of the peptide. In other embodiments, the E.W.G. can be bonded to a side chain if the peptide moiety.

Peptides can have a repeating backbone structure with side chains extending from the backbone units. Generally, each backbone unit has a side chain associated with it, although in some cases, the side chain is a hydrogen atom. In other embodiments, not every backbone unit has an associated sidechain. Peptides useful in peptide epoxides or peptide aziridines have two or more backbone units. In some embodiments useful for inhibiting chymotrypsin-like (CT-L) activity of the proteasome, between four and eight backbone units are present, and in some preferred embodiments for CT-L inhibition, between four and six backbone units are present. In other embodiments useful for inhibiting the PGPH activity of the proteasome, between two and eight backbone units are present, and in some preferred embodiments for PGPH inhibition, between three and six backbone units are present.

The side chains extending from the backbone units can include natural aliphatic or aromatic amino acid side chains, such as hydrogen (glycine), methyl (alanine), iso-propyl (valine), sec-butyl (isoleucine), iso-butyl (leucine), phenyl-methyl (phenylalanine), and the side chain constituting the amino acid proline. The side chains can also be other branched or unbranched aliphatic or aromatic groups such as ethyl, n-propyl, n-butyl, t-butyl, and aryl substituted derivatives such as 1-phenylethyl, 2-phenylethyl, (1-naphthyl)-methyl, (2-naphthyl)-methyl, 1-(1-naphthyl)ethyl, 1-(2-naphthyl)ethyl, 2-(1-naphthyl)ethyl, 2-(2-naphthyl)ethyl, and similar compounds. The aryl groups can be further substituted with branched or unbranched $C_{1-6}$ alkyl groups, or substituted alkyl groups, such as acetyl and the like, or further aryl groups, or substituted aryl groups, such as benzoyl and the like. Heteroaryl groups can also be used as side chain substituents. Heteroaryl groups include nitrogen-, oxygen-, and sulfur-containing aryl groups such as thienyl, benzothienyl, naphthothienyl, thianthrenyl, furyl, pyranyl, isobenzofuranyl, chromenyl, pyrrolyl, imidazolyl, pyrazolyl, pyridyl, pyrazinyl, indolyl, purinyl, quinolyl, and the like.

In some embodiments, polar or charged residues can be introduced into the peptide epoxides or peptide aziridines. For example, naturally occurring amino acids such as hydoxy-containing (Thr, Tyr, Ser) or sulfur-containing (Met, Cys) can be introduced, as well as non-essential amino acids, for example taurine, carnitine, citrulline, cystine, ornithine, norleucine and others. Non-naturally occurring side chain substituents with charged or polar moieties can also be included, such as, for example, $C_1$–$C_6$ alkyl chains or $C_6$–$C_{12}$ aryl groups with one or more hydroxy, short chain alkoxy, sulfide, thio, carboxyl, ester, phospho, amido or amino groups, or such substituents substituted with one or more halogen atoms. In some preferred embodiments, there is at least one aryl group present in a side chain of the peptide moiety.

In some embodiments, the backbone units are amide units [—NH—CHR—C(=O)—], in which R is the side chain. Such a designation does not exclude the naturally occurring amino acid proline, or other non-naturally occurring cyclic secondary amino acids, which will be recognized by those of skill in the art.

In other embodiments, the backbone units are N-alkylated amide units (for example. N-methyl and the like), olefinic analogs (in which one or more amide bonds are replaced by olefinic bonds), tetrazole analogs (in which a tetrazole ring imposes a cis-configuration on the backbone), or combinations of such backbone linkages. In still other embodiments, the amino acid α-carbon is modified by α-alkyl substitution, for example, aminoisobutyric acid. In some further embodiments, side chains are locally modified, for example, by $\Delta^E$ or $\Delta^Z$ dehydro modification, in which a double bond is present between the α and β atoms of the side chain, or for example by $\Delta^E$ or $\Delta^Z$ cyclopropyl modification, in which a cyclopropyl group is present between the α and β atoms of the side chain. In still further embodiments employing amino acid groups, D-amino acids can be used. Further embodiments can include side chain-to-backbone cyclization, disulfide bond formation, lactam formation, azo linkage, and other modifications discussed in "Peptides and Mimics, Design of Conformationally Constrained" by Hruby and Boteju, in "Molecular Biology and Biotechnology: A Comprehensive Desk Reference", ed. Robert A. Meyers, VCH Publishers (1995), pp. 658–664, which is hereby incorporated by reference.

The enzyme inhibitors for inhibition of chymotrypsin-like (CT-L) activity of Ntn include at least four backbone units. In some particularly preferred CT-L inhibitor embodiments, at least four amide units and an α',β'-epoxy ketone or α',β'-aziridine ketone moiety are present (tetrapeptide epoxy ketones or tetrapeptide aziridine ketones). In particular CT-L inhibitor embodiments with at least four amide units, the peptide moiety, and the ketone and epoxide or aziridine functionalities of the enzyme inhibitors form compounds with the general structure I:

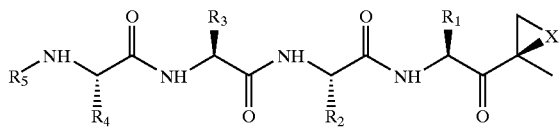

where X is oxygen, NH, or N-alkyl, $R_1$, $R_2$, $R_3$ and $R_4$ are independently selected from the group consisting of branched or unbranched $C_{1-6}$ alkyl or branched or unbranched $C_{1-6}$ hydroxy alkyl or branched or unbranched $C_{1-6}$ alkoxy alkyl, aryl, and aryl-substituted branched or unbranched $C_{1-6}$ alkyl, wherein such groups can further include: amide linkages; amines; carboxylic acids and salts thereof; carboxyl esters, including $C_{1-5}$ alkyl esters and aryl esters; thiols and thioethers; and $R_5$ is a further chain of amino acids, hydrogen, acetyl, or a protecting group, such as N-terminal protecting groups known in the art of peptide syntheses, including t-butoxy carbonyl (BOC), betizoyl (Bz), fluoren-9-ylmethoxycarbonyl (Fmoc), triphenylmethy (trityl) and trichloroethoxycarbonxyl (Troc) and the like. The use of various N-protecting groups, e.g., the benzyloxy carbonyl group or the t-butyloxycarbonyl group (BOC), various coupling reagents, e.g., dicyclohexylcarbodiimide, 1,3-diisopropylcarbodiimide (DIC), 1-(3-dimethylaminopropyl)-3-ethylcarbodiimide (EDC), N-hydroxyazabenzotriazole (HATU), carbonyldiimidazole, or 1-hydroxybenzotriazole monohydrate (HBT), and various cleavage reagents: for example, trifluoroacetic acid; HCL in dioxane; hydrogenation on Pd-C in organic solvents, such as methanol or ethyl acetate; boron tris(trifluoroacetate); and cyanogen bromide, and reaction in solution with isolation and purification of intermediates is well-known classical peptide methodology.

In some embodiments of chymotrypsin-like activity inhibitors, $R_1$ is branched or unbranched $C_{1-6}$ alkyl. In some embodiments of chymotrypsin-like activity inhibitors, $R_1$ is isobutyl. In some embodiments of chymotrypsin-like activity inhibitors, $R_2$ is branched or unbranched $C_{1-6}$ alkyl or aryl. In some embodiments of chymotrypsin-like activity inhibitors, $R_2$ is phenyl, phenylmethyl, or 1-naphthyl. In some embodiments of chymotrypsin-like activity inhibitors, $R_3$ is branched or unbranched $C_{1-6}$ alkyl or aryl. In some embodiments of chymotrysin-like-activity-inhibitors, $R_3$ is isobutyl, phenyl or 1-naphthyl. In some embodiments of chymotrypsin-like activity inhibitors, $R_4$ is branched or unbranched $C_{1-6}$ alkyl or aryl, and aryl-substituted branched or unbranched $C_{1-6}$ alkyl.

In some embodiments of chymotrypsin-like activity inhibitors, $R_4$ is isobutyl, phehyl, 1-naphthyl, phenylmethyl, or 2-phenylethyl. In some embodiments of chymotrypsin-like activity inhibitors, $R_5$ is hydrogen, $C_{1-6}$ alkanoyl, substituted or unsubstituted aryl, substituted or unsubstituted heteroaryl, where substituents include halogen, carbonyl, nitro, hydroxy, aryl, and $C_{1-5}$ alkyl. In some embodiments of chymotrypsin-like activity inhibitors, $R_5$ is hydrogen, acetyl, substituted or unsubstituted aryl.

In some preferred embodiments of chymotrypsin-like activity inhibitors, simultaneously, $R_1$ is isobutyl, $R_2$ is phenylmethyl, $R_3$ is isobutyl, and $R_4$ is 2 phenylethyl, and $R_5$ is acetyl.

The above definitions of R groups further include a proviso that, simultaneously. $R_1$ is not iso-butyl, $R_2$ is not 1-hydroxyethyl, $R_3$ is not sec-butyl, $R_4$ is not sec-butyl, and $R_5$ is not acetyl.

In some embodiments of PGPH activity inhibitors, $R_1$ is hydrogen, branched or unbranched $C_{1-6}$ alkyl. In some embodiments of PGPH activity inhibitors, $R_1$ is isobutyl. In some embodiments of PGPH activity inhibitors, $R_2$ is hydrogen, branched or unbranched $C_{1-6}$ alkyl or aryl. In some embodiments of PGPH activity inhibitors, $R_2$ is phenyl, phenylmethyl, or 1-naphthyl. In some embodiments of PGPH activity inhibitors, $R_3$ is hydrogen, branched or unbranched $C_{1-6}$ cyclic alkylene bonded to the $R_3$ backbone unit. In some embodiments of PGPH activity inhibitors, $R_3$ is ethylene bonded to the amine of the $R_3$ amino acid backbone, such as would be the case for the amino acid proline. In some optional embodiments of PGPH activity inhibitors, $R_4$ is hydrogen, branched or unbranched $C_{1-6}$ alkyl, aryl, and aryl-substituted branched or unbranched $C_{1-6}$ alkyl. In some other optional embodiments of PGPH activity inhibitors, $R_4$ is hydrogen, or isopropyl. In some optional embodiments of PGPH activity inhibitors, $R_5$ is hydrogen, $C_{1-6}$ alkanoyl, substituted or unsubstituted aryl, substituted or unsubstituted heteroaryl, where substituents include halogen, carbonyl, monosubstituted-, disubstituted- or unsubstituted-amino, nitro, hydroxy, aryl, and $C_{1-5}$ alkyl. In some optional embodiments of PGPH activity inhibitors, $R_5$ is acetyl, N-acetyl-piperidinecarbonyl, N-dimethylaminobenzyl, isooctanoic, or benzoylbenzoic.

In some preferred embodiments of PGPH activity inhibitors, simultaneously, $R_1$ is isobutyl, $R_2$ is phenyl, $R_3$ is ethylene bonded to the $R_3$ amine of the amino acid backbone, and $R_4$ is hydrogen, and $R_5$ is acetyl.

Selectivity for 20S Proteasome

The enzyme inhibitors disclosed herein are useful in part because they inhibit the action of the 20S proteasome. Additionally, unlike other 20S proteasome inhibitors, the compounds disclosed herein are highly selective toward the 20S proteasome, with respect to other protease enzymes. That is, the instant compounds show selectivities for the 20S proteasome over other proteases such as cathepsins, calpains, papain, chymotrypsin, trypsin, tripeptidyl pepsidase II. The selectivities of the enzyme inhibitors for 20S proteasome are such that at concentrations below about 50 µM, the enzyme inhibitors show inhibition of the catalytic activity of the 20S proteasome, while not showing inhibition of the catalytic activity of other proteases such as cathepsins, calpains, papain, chymotrypsin, trypsin, tripeptidyl pepsidase II. In preferred embodiments, the enzyme inhibitors show inhibition of the catalytic activity of the 20S proteasome at concentrations below about 10 µM, while not showing inhibition of the catalytic activity of other proteases at these concentrations. In even more preferred embodiments, the enzyme inhibitors show inhibition of the catalytic activity of the 20S proteasome at concentrations below about 1 µM, while not showing inhibition of the catalytic activity of other proteases at these concentrations. The enzyme kinetic assays are carried out as described below in Example 2.

Selectivity for Chymotrypsin-Like Activity

Particular embodiments of the enzyme inhibiting compounds described herein are further useful because they can efficiently and selectively inhibit the chymotrypsin-like activity of the 20S proteasome, as compared to the trypsin-like, and PGPH activities. The chymotrypsin-like activity of 20S proteasome is characterized by cleavage of peptides in the immediate vicinity of large hydrophobic residues. In particular, the chymotrypsin-like activity of Ntn hydrolases can be determined by cleavage of a standard substrate. Examples of such substrates are known in the art. For example, a leucylleucylvalinyltyrosine derivative can be used. Particular enzyme inhibitors described herein can inhibit the chymotrypsin-like activity of 20S proteasome on standard substrates at least about 80-fold faster than lactacystin and at least about four-fold faster than clastolactacystin β-lactone. Particular peptide epoxides and peptide aziridines primarily inhibit chymotrypsin-like activity of 20S proteasome; the trypsin-like and PGPH activities were also inhibited at approximately 100-fold and 1000-fold slower rates, respectively. The enzyme kinetic assays are carried out as described below in Example 2.

Selectivity for PGPH Activity

Particular embodiments of the enzyme inhibiting compounds described herein are further useful because they can efficiently and selectively inhibit the PGPH activity of the 20S proteasome, as compared to the chymotrypsin-like, and trypsin-like activities. The PGPH activity of 20S proteasome is characterized by cleavage of peptides in the immediate vicinity of acidic residues. In particular, the PGPH activity of Ntn hydrolases can be determined by cleavage of a standard substrate. Examples of such substrates are known in the art. For example, a leucylleucylglutamate derivative can be used. Particular peptide epoxides and peptide aziridines primarily inhibit PGPH activity of 20S proteasome; the chymotrypsin-like activity was inhibited at approximately a 40-fold slower rate. The trypsin-like activity is generally very poorly inhibited by the inhibitors optimized for PGPH inhibiton. The enzyme kinetic assays are carried out as described below in Example 2.

The Synthesis of Peptide Epoxides and Peptide Aziridines

Peptide epoxides and peptide aziridines, [3H]-peptide epoxides, and [3H]-peptide aziridines, and biotinylated peptide epoxides and biotinylated peptide aziridines can be synthesized as described herein.

A general strategy for the synthesis of peptide epoxides and peptide aziridines involves the synthesis of a first molecular fragment (also referred to as a "left hand" fragment), the parallel synthesis of a second molecular fragment (also referred to as a "right hand" fragment), and the coupling of these fragments. The use of amino terminal-, carboxy terminal-, and side chain-protecting groups is involved in the synthetic procedure. Any generally useful protecting groups can be used for the purposes of this synthesis. A number of amino terminal-, carboxy terminal-, and side chain-protecting groups are known to those of skill in the art. A key step is the removal of protecting groups while keeping the epoxide or aziridine ring intact. Additionally, the epoxide or aziridine ring can be introduced when a carbonyl group is present.

The synthesis of the first molecular fragment can begin with the reaction of an amino terminal protected amino acid with a carboxy terminal-protected amino acid to make a dipeptide with amino terminal and carboxy terminal protected. Any natural or non-natural amino acid can be used. For example, the synthesis of epoxomicin would involve reaction of amino terminal-protected isoleucine and carboxy terminal-protected threonine. Amino terminal- and carboxy terminal-protecting groups, as well as conditions and reagents for carrying out the reaction to make a dipeptide, are known to those in the art. For example, fluoren-9-ylmethoxycarbonylisoleucine (Fmoc-Ile-OH) can be coupled to threonine benzyl ester (H-Thr-OBn) with O-benzotriazo-1-yl -N,N,N',N'-tetramethyluronium hexafluorophosphate (HBTU) and 1-hydroxybenzotriazole (HOBt) in the presence of a relatively hindered base (for example, i-Pr$_2$NEt) in a non-polar, non-protic solvent (for example, CH$_2$Cl$_2$), at moderate temperature (for example, room temperature) for at least about 4 hours (for example 24 hours) to give dipeptide Fmoc-Ile-Thr-OBn in good yield (for example 79%).

In some embodiments, this step is followed by protection of a side chain hydroxyl group. For example, the synthesis of epoxomicin would involve protection of the side chain of threonine at this point. Hydroxyl side chain protecting groups are known in the art. For example, reaction of dipeptide Fmoc-Ile-Thr-OBn with t-butyldiphenylsilylchloride (TBDPSCl) in the presence of a base (for example, imidazole) in a non-protic solvent (for example, tetrahydrofuran) at a moderate temperature (for example, room temperature), for at least about 10 hours (for example, for 48 hours) yields a TBDPSCl-protected threonine side chain in Fmoc-Ile-Thr-OBn in moderate yield (for example, 64%).

If a hydroxyl-containing side chain is not involved, the above step can be omitted, or postponed until a later point. In any event, at this point, the amino terminal-protecting group is removed, by methods known in the art. For example, in an epoxomicin synthesis, Fmoc can be removed by reaction in the presence of a base (for example, piperidine) in a polar, non-protic solvent (for example, dimethylformamide), at a moderate temperature (for example, room temperature), for at least about five minutes (for example 20 minutes) to give the amino terminal deprotected H-Ile-Thr-OBn (with Thr side chain protected, as detailed above) in near-quantitative yield.

At this point, a third amino acid is coupled to the amino terminus of the dipeptide to make an amino terminal- and carboxy terminal-protected tripeptide. As above, conditions and reagents for this coupling reaction are known in the art. For example, for an epoxomicin synthesis, reaction of Fmoc-N-methyl-isoleucine (Fmoc-MeIle-OH) with H-Ile-Thr-OBn (with Thr side chain protected) in the presence of coupling reagents O-benzotriazo-1-yl-N,N,N',N'-tetramethyluronium hexafluorophosphate (HBTU) and 1-hydroxybenzotriazole (HOBt) in the presence of a relatively hindered base (for example, i-Pr$_2$NEt) in a non-polar, non-protic solvent (for example, CH$_2$Cl$_2$), at moderate temperature (for example, room temperature) for at least about 4 hours (for example 18 hours) to give tripeptide Fmoc-MeIle-Ile-Thr-OBn in near-quantitative yield (for example 99%).

Acetylation of the amino terminus is then carried out, by reaction of exemplary tripeptide Fmoc-X$_1$-X$_2$-X$_3$-OBn with an acetylating agent, where X$_1$, X$_2$, and X$_3$ are amino acids, to give exemplary acetylated tripeptide Ac-X$_1$-X$_2$-X$_3$-OBn. For example. for an epoxomicin synthesis. acetylation of Fmoc-MeIle-Ile-Thr-OBn is carried out with an acetylating agent (for example, acetic anhydride) in the presence of a relatively hindered base (for example, i-Pr$_2$NEt) in a nonpolar, non-protic solvent (for example, CH$_2$Cl$_2$), at moderate temperature (for example, room temperature) for at least about 1 hour (for example 3.5 hours) to give tripeptide Ac-MeIle-Ile-Thr-OBn in near-quantitative yield (for example 99%).

Catalytic hydrogenation of exemplary acylated tripeptide Ac-X$_1$-X$_2$-X$_3$-OBn removes the carboxyl terminus protecting group to give exemplary tripeptide Ac-X$_1$-X$_2$-X$_3$-OH. For example, for an epoxomicin synthesis, hydrogenation of Ac-MeIle-Ile-Thr-OBn by a typical catalytic hydrogenation agent (for example, 10% Pd-C) in the presence of hydrogen gas removes the benzyl ester to yield the free carboxyl terminus in Ac-MeIle-Ile-Thr-OH in essentially quantitative yield. At this stage the first ("left hand") molecular fragment is completed.

The second ("right hand") molecular fragment can be made in parallel or in sequence. This procedure involves alkenylating a Weinreb amide of an amino terminal protected amino acid. For example, an amino terminal protected amino acid can be reacted with a reagent (for example, MeNHOMe×HCl, EDCl, NMM, HoBt, DMF, 0°, 12 h, 80%) to make a Weinreb amide of the carboxyl terminus of the amino acid. Alkenylation is carried out by exposing the Weinreb amide to an alkenylating agent (for example, propen-2-yl lithium) to give an α',β'-unsaturated ketone. For example, for an epoxomicin synthesis, Boc-Leu Weinreb amide can be reacted with propen-2-yl lithium to give the corresponding α',β'-unsaturated ketone. Propen-2-yl lithium can be generated by reaction of 2-bromopropene with t-butyl lithium in a non-protic solvent (for example, diethyl ether) at low temperature (for example −78° C.), for at least 30 minutes (for example 2.5 hours) to give the α',β'-unsaturated ketone in excellent yield (for example, 92%).

At this point, the α',β'-unsaturated ketone can be epoxidized to form an α',β'-epoxy ketone; alternatively, nitrogen can be added to the α',β'-unsaturated ketone to form an α',β'-aziridine ketone. Nitrogen can be added by thermal or photochemical reaction with an azide (RN$_3$ where R is aryl, cyano, EtOOC and alkyl-SO$_2$, as well as other groups). For example, for an epoxomicin synthesis, a typical epoxidizing reagent (for example, alkaline hydrogen peroxide) can be reacted with the α',β'-unsaturated ketone described above, in polar solvent (for example, aqueous solution or methanol in water) in the presence of a compound which gives a reactive intermediate, which reacts with the unsaturated ketone to give an epoxide product (for example, benzonitrile), and a moderately hindered base (for example, i-Pr$_2$Net) at moderately low temperature (for example, 0 to 4° C.), for at least about 10 hours (for example, 43 hours) to give the α',β'-epoxy ketone in good yield (for example, 76%).

In another embodiment, an α',β'-aziridine ring can be introduced by forming an epoxide ring substantially as disclosed above, opening the epoxide ring to give a tertiary alcohol, using acid catalysis, base catalysis, specific catalysis, or any other technique known to those of skill in the art. Thereafter, substituting the alcohol with a suitable leaving group, such as tosylate, for example, and addition of an azide, such as an alkali or alkali metal salt of an azide, can result in an aziridine ring.

In yet another embodiment, an α',β'-aziridine ring can be introduced by way of an enolate reaction, as follows. A peptide, protected at the carboxy terminus with an ester group, such as a branched or unbranched C$_{1-6}$ alkyl ester, for example a methyl ester, is reacted with a halogenated alkylating agent. Such halogenated alkylating agents include, for example 1-halo-1-metalloalkanes, including 1-bromo-1-lithio-ethane. These reagents can be generated according to methods known in the art, such as by treating a dihalogenated alkane with an alkylating reagent such as n-butyllithium in a nonpolar, nonprotic solvent such as diethyl ether, at low temperature, for example -78° C. The reaction between the esterified peptide and the halogenated alkylating agent results in an α-haloketone, which is substantially racemic at the α carbon.

The α-haloketone is treated, in the presence of an base (such as a nitrogenous base, for example, triethylamine), with a boron-containing reagent such as XBL*$_2$ where X is halogen, B is boron, and L* is an H. C. Brown chiral auxiliary ligand, (for example, diisopinocanpheyl; IPC) further examples of which are well known to those of skill in the art. The selection of chiral auxiliary ligand can be used to produce high stereoselectivity in aziridine formation. Such stereoselectivity can simplify purification procedures. It is believed that particular aziridine and epoxide stereoisomers can possess superior utility for some applications.

The α-haloketone can alternatively be treated, in the presence of an base (such as a nitrogenous base, for example, triethylamine), with a dialkyl boron reagent having a leaving group bonded to boron. This reagent can take the form YBR$_2$''', where Y is a leaving group, for example, triflate, B is boron, and R''' can be aryl, heteroaryl, or branched or unbranched C$_{1-6}$ alkyl, any of which can be further substituted with halogen, hydroxy, amine, aryl, thiol, sulfide, ether, ester, amide or nitro groups. B can alternatively be bonded to a single group which forms a cyclic ligand, such as, for example, the alkylene —(CH$_2$)$_n$—where n is from 2 to 7 for example. Such groups can be further substituted as described immediately above.

The product of the reaction of the α-haloketone with either of these types of reagents is then treated with an imine in a nonpolar, nonprotic solvent such as diethyl ether, at a low temperature, for example, −78° C. and raised to a more moderate temperature, for example, room temperature, over a time period of at least about 4 hours, for example, from about 4 hours to about 18 hours. The imine can be of the form H$_2$C=N—Z, where Z can be a silyl, for example, trialkylsilyl, triarylsilyl, or any combination of three alkyl or aryl silicon substituents, for example, trimethylsilyl, or triisopropylsilyl; Z can also be a sulfonyl, for example, alkylsulfonyl or arylsulfonyl, for example benzenesulfonyl. As the reaction mixture temperature approaches a moderate temperature, the reaction mixture is treated with a basic solution of excess hydrogen peroxide, sodium perborate, or similar workup reagent to yield the aziridine. A general scheme is given below.

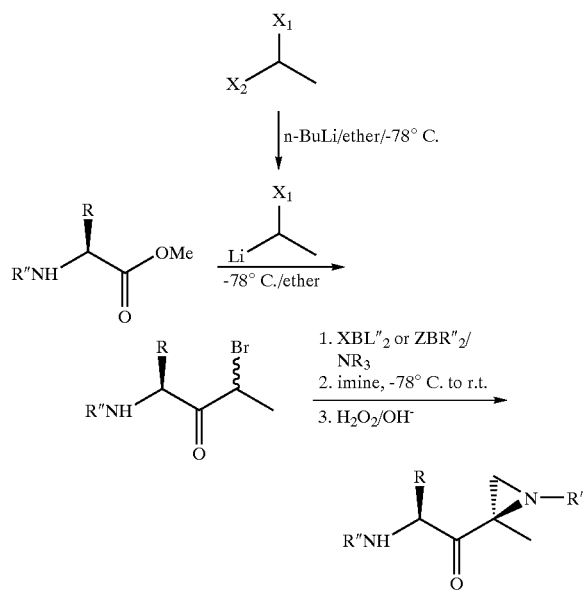

where Z is as described above, X, X$_1$ and X$_2$ are independently halogens, R can be branched or unbranched alkyl, aryl, heteroaryl, including such groups substituted with hydroxy, halogen, amide, ester, amine, ether, sulfide, and thiols. In particular embodiments, R is a branched or unbranched aliphatic or aromatic group such as ethyl, n-propyl, n-butyl, t-butyl, and aryl substituted derivative such as 1-phenylethyl, 2-phenylethyl, (1-naphthyl)-methyl, (2-naphthyl,)-ethyl, 1-(1-naphthyl)ethyl, 1-(2-naphthyl) ethyl, 2-(1-naphthyl)ethyl, 2-(2-naphthyl,)-methyl, and similar compounds. The aryl groups can be further substituted with branched or unbranched C$_{1-6}$ alkyl groups, or substituted alkyl groups, such as acetyl and the like, or further aryl groups, or substituted aryl groups, such as benzoyl and the like. Heteroaryl groups can also be used as R. Heteroaryl groups include nitrogen-, oxygen-, and sulfur-containing aryl groups such as thienyl, benzothienyl, naphthothienyl, thianthrenyl, furyl, pyranyl, isobenzofuranyl, chromenyl, pyrrolyl, imidazolyl, pyrazolyl, pyridyl, pyrazinyl, indolyl, purinyl, quinolyl, and the like.

In some embodiments, polar or charged residues can be used as R. For example, groups corresponding to the side chains of naturally occurring amino acids such as hydoxy-containing (Thr, Tyr, Ser) or sulfur-containing (Met, Cys) can be used, as well as those corresponding to the side chains of non-essential amino acids, for example taurine, carnitine, citrulline, cystine, ornithine, norleucine and others. Non-naturally occurring substituents with charged or polar moieties can also be included, such as, for example, C$_1$–C$_6$ alkyl chains or C$_6$–C$_{12}$ aryl groups with one or more hydroxy, short chain alkoxy, sulfide, thio, carboxyl, ester, phospho, amido or amino groups, or such substituents substituted with one or more halogen atoms.

R''' can be any group as described above with respect to the boron-containing reagent. R'' can be branched or unbranched alkyl, aryl, heteroaryl, including such groups substituted with hydroxy, halogen, amide, ester, amine, ether, sulfide, and thiols. In particular embodiments, R''' can be a peptide such as a dipeptide, tripeptide, tetrapeptide and so forth, having side chains as described above with respect to enzyme inhibitors, and R' is the group derived from the imine, for example a silyl or sulfonyl group such as trimethylsilyl or benzenesulfonyl. The R' group can be converted to hydrogen by treatment with a reagent such as TBAF (tetrabutylammonium fluoride) in a solvent suitable for such conversion. R' can be converted to alkyl by treatment with an S$_N$2 substrate such as an alkyl halide, in solvents suitable for such conversion.

The introduction of an epoxide or aziridine ring at this stage makes the α' carbon chiral. Generally, some significant amount of each stereoisomer is formed at this stage. For example, in the above synthesis of epoxomicin using Boc-protected Leu, the ratio of compound having the (R) α' carbon to the compound having the (S) α' carbon was 1.7:1. The same synthesis using Z-protected Leu gave a 4.0:1 (R):(S) ratio. These compounds were readily separated, for example by flash chromatography, in common solvent systems, for example hexanes:EtOAc 10:1). In some embodiments, the R stereoisomer (as described above, with peptide-E.W.G. attached from the left, and R attached from the right, the X atom projects above the plane of the page) is a preferred isomer, and further reactions were carried out with that isomer.

At this stage, the amino terminal protection group of the α',β'-epoxy ketone or α',β'-aziridine ketone is removed, but without disturbing the epoxide or aziridine ring. For example, if the amino terminal protecting group is Boc, brief treatment of the α',β'-epoxy ketone or the α',β'-aziridine ketone with a deprotection agent (for example, trifluoroacetic acid), at a moderate temperature (for example, room temperature) for a short time (for example, from about 2 to about 20 minutes, preferably from about 3 to about 18 minutes, more preferably from about 5 to about 15 minutes, and even more preferably, about 10 minutes) gives the second molecular fragment in excellent yield. Under these conditions of trifluoroacetic acid treatment, there are no very good nucleophiles available to attack the epoxide or aziridine. The deprotected amine is immediately able to form a trifluoroacetate salt, which is a good leaving group. Even if trifluoroacetate were to open the three-membered, heteroatom-containing ring, the reverse reaction is generally more favorable.

At this stage, the second molecular fragment is completed and can be coupled to the first molecular fragment. For example, reaction of the first and second molecular fragments with O-benzotriazo-1-yl-N,N,N',N'-tetramethyluronium hexafluorophosphate (HBTU) and 1-hydroxybenzotriazole (HOBt) in the presence of a relatively hindered base (for example, i-Pr$_2$NEt) in a non-polar, non-protic solvent (for example, CH$_2$Cl$_2$), at moderate temperature (for example, room temperature) for at least about 4 hours (for example 18 hours) to give a tetrapeptide epoxy ketone or tetrapeptide aziridine ketone in moderate yield (for example 48%). If a hydroxyl side chain has been introduced, its protecting group will be removed at this stage.

For example, for an epoxomicin synthesis, reaction of the first molecular fragment, Ac-MeIle-Ile-Thr-OH (with Thr side chain protected, as described above), with the second molecular fragment derived from H-Leu-α', β'-epoxy ketone and a fluorinating agent (for example, tetrabutylammonium fluoride; TBAF), in a non-protic solvent (for example, tetrahydrofuran; THF), at a moderate temperature (for example, room temperature), for at least about 10 minutes (for example, 1 hour), gives epoxomicin in excellent yield (for example, 96%).

Peptide epoxides and peptide aziridines are also readily amenable to synthesis and derivativization via solid phase syntheses. Commercially available solid state synthetic supports, such as for example, chlorinated resins, including 2-chlorotrityl chloride resin (available from Advanced Chemtech) can be treated with N-terminal protected amino acids. For the case of hydroxy-side chain-containing amino acids, the hydroxy-side chain can also be desirably protected. Standard peptide synthesis conditions can be utilized to elongate the peptide chain. The peptide can be readily detached from the solid support by known methods, including for example, acetic acid/trifluoromethanol/dichloromethane in a ratio of approximately 1:1:3 ratio, at a moderate temperature, for example room temperature, for at least about 20 minutes, for example for 2 hours. The detached peptide can then be coupled to a "right hand" molecular fragment, and further reacted with reagents to give peptide epoxides and peptide aziridines, as described above.

In order to synthesize peptide epoxides and peptide aziridines with tritiated acetylene at the N-terminal position, an N-protected tetrapeptide-epoxide or -aziridine, as described above is reacted with a base, such as piperidine in a polar solvent, such as dimethylformamide, at a moderate temperature, for example, room temperature, for at least about 2 minutes, for example, 20 minutes. The resulting amine is reacted with a tritiating agent which can react with an amino terminus, for example, [3H]-acetic anhydride in a non-polar solvent, for example, methylene chloride, in the presence of a base, for example diisopropylamine, at a moderate temperature, for example, room temperature, for at least one hour, for example, 8 hours. Concentration and chromatography yields a protected tritiated peptide epoxide or peptide aziridine, which can be deprotected according to methods known in the art.

Biotinylated peptide epoxides and aziridines can be prepared by providing an N-terminal protected, C-terminal protected, and if necessary, hydroxy-side chain protected left hand molecular fragment (described above), reacting this fragment with a base such as a nitrogenous base, for example, piperidine, in a non-protic solvent, for example, tetrahydrofuran, at a moderate temperature, for example, room temperature, for at least about 6 hours, for example, 26 hours, to give an intermediate amine product in good yield, for example about 91%. The intermediate amine product is reacted with an amino-protected aminoalkanoic acid, such as N-Fmoc-6-aminohexanioc acid in the presence of an activating agent such as benzotriazolyl N-oxytrisdimethylamino-phosphonium hexafluorophosphate (BOP), bromo-tris-pyrrolidino-phosphonium-hexafluorophosphate (PyBrop), benzotriazole-1-yl-oxy-tris-pyrrolidino-phosphonium-hexafluorophosphate (PyBOP), O-benzotriazole-N,N,NÕ,NÕ-tetramethyluronium hexafluoro-phosphate (HBTU), 2-(1H-benzotriazole-1-yl)-1,1,3, 3-tetramethyluronium tetrafluoroborate (TBTU), or O-(7-azabenzotriazole-1-yl)-1,1,3,3-tetramethyluronium tetrafluorophosphate (HATU). All of the previously named reagents require activating bases, such as for example, hindered nitrogenous bases such as diisopropylethylamine. The reaction is carried out in a non-polar solvent such as methylene chloride, at a moderate temperature, such as room temperature, for at least about 10 minutes, for example, 2 hours, to give a spacer deriviative in excellent yield, for example 98%. The C-terminal protecting group, for example, a benzyl ester, is removed, for example, by treatment with 10% Pd—C and $H_2$.

Coupling of the C-terminal deprotected left hand fragment with a right hand molecular fragment (as described above), with for example, HATU/HOAt, in the presence of a nitrogenous base, such as diisopropylethylamine, in a nonpolar solvent, for example, methylene chloride, at a moderate temperature, such as room temperature, for at least about 4 hours, for example 22 hours, yields an amino-protected peptide epoxide or amino-protected peptide aziridine in acceptable yield, for example, 60%. Simultaneous removal of the amino-terminal and, if present, hydroxy side chain protecting groups, for example by treatment with TBAF in THF at room temperature for at least about 10 minutes, for example 1 hour, is followed by N-acylation with commercially available N-(N-biotinyl-6-aminohexanoyl)-6-aminohexanoic acid succinimidyl ester (Biotin-X-X-NHS) in a polar, non-protic solvent, for example, DMSO, at a moderate temperature, for example, room temperature, for at least about 2 hours, for example, for 24 hours, gives a biotinylated peptide epoxide or biotinylated peptide aziridine in good yield, for example 87%.

Uses of Enzyme Inhibitors

Using epoxomicin and its biotinylated affinity derivative, we show that epoxomicin covalently binds the LMP7, X, Z, and MECL1 catalytic β subunits of the 20S proteasome and selectively inhibits the three major 20S proteasome proteolytic activities at different rates. Evidence is presented in vitro and in vivo that epoxomicin effectively inhibits NF-κB-mediated pro-inflammatory signaling. Given its unique specificity and potency, these antitumor, anti-inflammatory natural products represent novel classes of irreversible inhibitors distinct from those reagents currently in use and, thus, might prove useful in in vivo and in vitro analyses of proteasome function.

Peptide epoxides and peptide aziridines can inhibit NF-κB activation, and stabilize p53 levels in cell culture. Since NF-κB is a key regulator of inflammation, it is an attractive target for anti-inflammatory therapeutic intervention. While several peptide aldehyde proteasomal inhibitors have been shown to target NF-κB activation, their potential cross-reactivity with other cellular proteases limits their usefulness in studying the biological processes of proteasome function and also raises concerns for their use in studying pathological disease processes. In comparison to these other proteasome inhibitors, peptide epoxides and peptide aziridines are unique, demonstrating potent and specific inhibition of the proteasome and its functions.

The biological consequences of proteasome inhibition are numerous. At the cellular level, the accumulation of polyubiquitinated proteins, cell morphological changes, and apoptosis have been reported upon treatment of cells with various proteasome inhibitors. In our analyses, we have observed that p53 levels are stabilized over 50-fold by epoxomicin treatment. In addition, our results showing an accumulation of polyubiquitinated proteins in epoxomicin-treated cells provide evidence that the proteasome is the target of epoxomicin. Proteasome inhibition has also been suggested as a possible antitumor therapeutic strategy. The fact that epoxomicin was initially identified in a screen for antitumor compounds validates the proteasome as an antitumor chemotherapeutic target. Moreover, in parallel with this study, we have found that another antitumor natural product, eponemycin, targets the proteasome, however, less potently.

The disclosed compounds are used to treat conditions mediated directly by the proteolytic function of the proteasome such as muscle wasting, or mediated indirectly via proteins which are processed by the proteasome such as NF-κB. The proteasome participates in the rapid elimination and post-translational processing of proteins (e.g., enzymes) involved in cellular regulation (e.g., cell cycle, gene transcription, and metabolic pathways), intercellular communication, and the immune response (e.g., antigen presentation). Specific examples discussed below include β-amyloid protein and regulatory proteins such as cyclins and transcription factor NF-κB.

Alzheimer's disease is characterized by extracellular deposits of β-amyloid protein (β-AP) in senile plaques and cerebral vessels. β-AP is a peptide fragment of 39 to 42 amino acids derived from an amyloid protein precursor (APP). At least three isoforms of APP are known (695, 751, and 770 amino acids). Alternative splicing of mRNA generates the isoforms; normal processing affects a portion of the β-AP sequence, thereby preventing the generation of β-AP. It is believed that abnormal protein processing by the proteasome contributes of the abundance of β-AP in the Alzheimer brain. The APP-processing enzyme in rats contains about ten different subunits (22 kDa-32 kDa). The 25 kDa subunit has an N-terminal sequence of X-Gln-Asn-Pro-Met-X-Thr-Gly-Thr-Scr (SEQ ID NO:2), which is identical to the β-subunit of human macropain (Kojima, S. et al., Fed. Eur. Biochem. Soc., (1992) 304:57–60). The APP-processing enzyme cleaves at the $Gln^{15}$--$Lys^{16}$ bond; in the presence of calcium ion, the enzyme also cleaves at the $Met^{-1}$--$Asp^1$ bond, and the $Asp^1$--$Ala^2$ bonds to release the extracellular domain of β-AP.

One embodiment, therefore, is a method of treating Alzheimer's disease, including administering to a subject an effective amount of a compound (e.g., pharmaceutical composition) disclosed herein. Such treatment includes reducing the rate of β-AP processing, reducing the rate of β-AP plaque formation, and reducing the rate of β-AP generation, and reducing the clinical signs of Alzheimer's disease.

Other embodiments of the invention relate to cachexia and muscle-wasting diseases. The proteasome degrades many proteins in maturing reticulocytes and growing fibroblasts. In cells deprived of insulin or serum, the rate of proteolysis nearly doubles. Inhibiting the proteasome reduces proteolysis, thereby reducing both muscle protein loss and the nitrogenous load on kidneys or liver. Proteasome inhibitors are useful for treating conditions such as cancer, chronic infectious diseases, fever, muscle disuse (atrophy) and denervation, nerve injury, fasting, renal failure associated with acidosis, and hepatic failure. See, e.g., Goldberg, U.S. Pat. No. 5,340,736. Embodiments of the invention therefore encompass methods for: reducing the rate of muscle protein degradation in a cell; reducing the rate of intracellular protein degradation; reducing the rate of degradation of p53 protein in a cell; and inhibiting the growth of p53-related cancers. Each of these methods includes the step of contacting a cell (in vivo or in vitro, e.g., a muscle in a subject) with an effective amount of a compound (e.g., pharmaceutical composition) disclosed herein.

Another protein processed by the proteasome is NF-κB, a member of the Rel protein family. The Rel family of transcriptional activator proteins can be divided into two groups. The first group requires proteolytic processing, and includes p50 (NF-κB1, 105 kDa) and p52 (NF-κ2, 100 kDa). The second group does not require proteolytic processing, and includes p65 (RelA, Rel (c-Rel), and RelB). Both homo- and heterodimers can be formed by Rel family members; NF-κB, for example, is a p50-p65 heterodimer. After phosphorylation and ubiquitination of IκB and p105, the two proteins are degraded and processed, respectively, to produce active NF-κB which translocates from the cytoplasm to the nucleus. Ubiquitinated p105 is also processed by purified proteasomes (Palombella et al., Cell (1994) 78:773–785). Active NF-κB forms a stereospecific enhancer complex with other transcriptional activators and, e.g., HMG I(Y), inducing selective expression of a particular gene.

NF-κB regulates genes involved in the immune and inflammatory response, and mitotic events. For example, NF-κB is required for the expression of the immunoglobulin light chain κ gene, the IL-2 receptor α-chain gene, the class I major histocompatibility complex gene, and a number of cytokine genes encoding, for example, IL-2, IL-6, granulocyte colony-stimulating factor, and IFN-β(Palombella et al., Cell (1994) 78:773–785). Some embodiments of the invention include methods of affecting the level of expression of IL-2, MHC-I, IL-6, IFN-β or any of the other previously-mentioned proteins, each method including administering to a subject an effective amount of a compound disclosed herein. Complexes including p50 are rapid mediators of acute inflammatory and immune responses (Thanos, D. and Maniatis, T., Cell (1995) 80:529–532).

NF-κB also participates in the expression of the cell adhesion genes that encode E-selectin, P-selectin, ICAm, and VCAM-1 (Collins, T., Lab. Invest. (1993) 68:499–508). One embodiment of the invention is a method for inhibiting cell adhesion (e.g., cell adhesion mediated by E-selectin, P-selectin, ICAm, or VCAM-1), including contacting a cell with (or administering to a subject) an effective amount of a compound (e.g., pharmaceutical composition) disclosed herein.

NF-κB also binds specifically to the HIV-enhancer/promoter. When compared to the Nef of mac239, the HIV regulatory protein Nef of pbj 14 differs by two amino acids in the region which controls protein kinase binding. It is believed that the protein kinase signals the phosphorylation of I-κB, triggering IκB degradation through the ubiquitin-proteasome pathway. After degradation, NF-κB is released into the nucleus, thus enhancing the transcription of HIV (Cohen, J., Science, (1995) 267:960). Two embodiments of the invention are a method for inhibiting or reducing HIV infection in a subject, and a method for decreasing the level of viral gene expression, each method including administering to the subject an effective amount of a compound disclosed herein.

Intracellular proteolysis generates small peptides for presentation to T-lymphocytes to induce MHC class I-mediated immune responses. The immune system screens for autologous cells that are virally infected or have undergone oncogenic transformation. One embodiment is a method for inhibiting antigen presentation in a cell, including exposing the cell to a compound described herein. A further embodiment is a method for suppressing the immune system of a subject (e.g., inhibiting transplant rejection), including administering to the subject an effective amount of a compound described herein.

Another further embodiment is a method for altering the repertoire of antigenic peptides produced by the proteasome or other Ntn with multicatalytic activity. For example, if the PGPH activity of 20S proteasome is selectively inhibited, a different set of antigenic peptides will be produced by the proteasome and presented in MHC molecules on the surfaces of cells than would be produced and presented either without any enzyme inhibition, or with, for example, selective inhibition of chymotrypsin-like activity of the proteasome.

Certain proteasome inhibitors block both degradation and processing of ubiquitinated NF-κB in vitro and in vivo. Proteasome inhibitors also block IκB-A degradation and NF-κB activation (Palombella, et al. *Cell* (1994) 78:773–785; and Traenckner, et al., *EMBO J.* (1994) 13:5433–5441). One embodiment of the invention is a method for inhibiting IκB-α degradation, including contacting the cell with a compound described herein. A further embodiment is a method for reducing the cellular content of NF-κB in a cell, muscle, organ, or subject, including contacting the cell, muscle, organ, or subject with a compound described herein.

Other eukaryotic transcription factors that require proteolytic processing include the general transcription factor TFIIA, herpes simplex virus VP16 accessory protein (host cell factor), virus-inducible IFN regulatory factor 2 protein, and the membrane-bound sterol regulatory element-binding protein 1.

Other embodiments of the invention are methods for affecting cyclin-dependent eukaryotic cell cycles, including exposing a cell (in vitro or in vivo) to a compound disclosed herein. Cyclins are proteins involved in cell cycle control. The proteasome participates in the degradation of cyclins. Examples of cyclins include mitotic cyclins, G1 cyclins, (cyclin B). Degradation of cyclins enables a cell to exit one cell cycle stage (e.g., mitosis) and enter another (e.g., division). It is believed all cyclins are associated with p34.sup.cdc2 protein kinase or related kinases. The proteolysis targeting signal is localized to amino acids 42-RAALGNISEN-50 (destruction box; SEQ ID NO:19). There is evidence that cyclin is converted to a form vulnerable to a ubiquitin ligase or that a cyclin-specific ligase is activated during mitosis (Ciechanover, A., Cell, (1994) 79:13–21). Inhibition of the proteasome inhibits cyclin degradation, and therefore inhibits cell proliferation, for example, in cyclin-related cancers (Kumatori et al., Proc. Natl. Acad. Sci. USA (1990) 87:7071–7075). One embodiment of the invention is a method for treating a proliferative disease in a subject (e.g., cancer, psoriasis, or restenosis), including administering to the subject an effective amount of a compound disclosed herein. The invention also encompasses a method for treating cyclin-related inflammation in a subject, including administerinig to a subject an effective amount of a compound described herein.

Addition of embodiments are methods for affecting the proteasome-dependent regulation of oncoproteins and methods of treating or inhibiting cancer growth, each method including exposing a cell (in vivo, e.g., in a subject or in vitro) to a compound disclosed herein. HPV-16 and HPV-18-derived E6 proteins stimulate ATP-and ubiquitin-dependent conjugation and degradation of p53 in crude reticulocyte lysates. The recessive oncogene p53 has been shown to accumulate at the nonpermissive temperature in a cell line with a mutated thermolabile E1. Elevated levels of p53 may lead to apoptosis. Examples of proto-oncoproteins degraded by the ubiquitin system include c-Mos, c-Fos, and c-Jun. One embodiment is a method for treating p53-related apoptosis, including administering to a subject an effective amount of a compound disclosed herein.

Finally, the disclosed compounds are also useful as diagnostic agents (e.g., in diagnostic kits or for use in clinical laboratories) for screening for proteins (e.g., enzymes, transcription factors) processed by Ntn hydrolases, including the proteasome. The disclosed compounds are also useful as research reagents for specifically binding the X/MB1 subunit or α-chain and inhibiting the proteolytic activities associated with it. For example, the activity of (and specific inhibitors of) other subunits of the proteasome can be determined.

Most cellular proteins are subject to proteolytic processing during maturation or activation. Enzyme inhibitors disclosed herein can be used to determine whether a cellular, developmental, or physiological process or output is regulated by the proteolytic activity of a particular Ntn hydrolase. One such method includes obtaining an organism, an intact cell preparation, or a cell extract; exposing the organism, cell preparation, or cell extract to a compound disclosed herein; exposing the compound-exposed organism, cell preparation, or cell extract to a signal, and monitoring the process or output. The high selectivity of the compounds disclosed herein permits rapid and accurate elimination or implication of the Ntn (for example, the 20S proteasome) in a given cellular, developmental, or physiological process.

Administration

The methods of the invention contemplate treatment of animal subjects, such as mammals (e.g., higher primates, and especially humans). The invention encompasses pharmaceutical compositions which include novel compounds described herein, and pharmaceutical compositions which include compounds described and first recognized herein as Ntn inhibitors, such as the peptide epoxides and peptide aziridines described herein.

Pharmaceutically acceptable salts may be formed, for example, with 1, 2, 3, or more equivalents of hydrogen chloride, hydrogen bromide, trifluoroacetic acid, and others known to those in the art of drug formulation. Compounds of the invention can be formulated into pharmaceutical compositions by admixture with pharmaceutically acceptable non-toxic excipients and carriers. A pharmaceutical composition of the invention may contain more than one compound of the invention, and/or may also contain other therapeutic compounds not encompassed by the invention, such as anti-inflammatory, anti-cancer, or other agents. A compound of the invention may be administered in unit dosage form, and may be prepared by any of the methods well known in the pharmaceutical art, for example, as described in Remington's Pharmaceutical Sciences (Mack Pub. Co., Easton, Pa., 1980). The invention also encompasses a packaged drug, containing a pharmaceutical composition formulated into individual dosages and printed instructions for self-administration.

Compounds disclosed herein as Ntn hydrolase inhibitors may be prepared for use in parenteral administration, particularly in the form of solutions or liquid suspensions; for oral administrations, particularly in the form of tablets or capsules, or intranasally, particularly in the form of powders, gels, oily solutions, nasal drops, aerosols, or mists. Formulations for parenteral administration may contain as common excipients sterile water or sterile saline, polyalkylene glycols such as polyethylene glycol, oils of vegetable origin, hydrogenated naphthalenes, and the like. Controlled release of a compound of the invention may be obtained, in part, by use of biocompatible, biodegradable polymers of lactide, and copolymers of lactide/glycolide or polyoxyethylene/polyoxypropylene. Additional parental delivery systems include ethylene-vinyl acetate copolymer particles, osmotic pumps, implantable infusion systems, and liposomes. Formulations for inhalation administration contain lactose, polyoxyethylene-9-lauryl ether, glycocholate, or deoxycholate. Formulations for buccal administration may include glycocholate; formulations for vaginal administration may include citric acid.

The concentration of a disclosed compound in a pharmaceutically acceptable mixture will vary depending on several factors, including the dosage of the compound to be administered, the pharmacokinetic characteristics of the compound(s) employed, and the route of administration. In general, the compounds of this invention may be provided in an aqueous physiological buffer solution containing about 0.1–10% w/v of compound for parenteral administration. Typical dose ranges are from about 0.01 to about 50 mg/kg of body weight per day, given in 1–4 divided doses. Each divided dose may contain the same or different compounds of the invention. The dosage will be an effective amount depending on several factors including the overall health of a patient, and the formulation and route of administration of the selected compound(s).

The effective amount of the active compound used to practice the present invention for treatment of conditions directly or indirectly mediate by Ntn hydolases varies depending upon the manner of administration, the age and the body weight of the subject and the condition of the subject to be treated, and ultimately will be decided by the attending physician or veterinarian. Such amount of the active compound as determined by the attending physician or veterinarian is referred to herein as "effective amount".

The invention will be further described in the following examples, which do not limit the scope of the invention described in the claims.

EXAMPLES

The following examples illustrate some advantages and properties of particular embodiments of the invention.

Materials and methods are generally described as follows. Streptavidin-1-IRP, and streptavidin agarose were purchased from Sigma. Suc-LLVY-AMC (SEQ ID NO:1), Boc-LRR-AMC CalBiochem, NeutrAvidin beads were from were purchased from Bachem. Z-LLE-AMC, elasto-lactacystin β-lactone, NLVS, calpain substrate I were obtained from CalBiochem. NeutrAvidin beads were from Pierce. Picrylchloride was a gift from Dr. Philip Asekanse, Yale University School of Medicine.

Cell culture and treatments are generally described as follows. 1-IUVE cells (generously provided by J. Pober, Yale University) were cultured in Dulbecco's minimal essential medium (DMEM, Gibco-BRL), containing 10% fetal bovine serum (FBS) and 50 µg/ml endothelial cell growth factor (Sigma). The transformed human kidney epithelial cell line (HEK-293) and Hela cell line were cultured in DMEM containing 10% FBS. The mouse thymoma cell line EL4 was cultured in RPMI (Gibco-BRL) plus 10% FBS. All cell culture media were supplemented with 50 µg/L penicillin and 50 µg/L streptomycin.

For aIκB western-blot analysis, 60% confluent monolayers were treated in duplicate with 10 µM epoxomicin for 2 hour in conjunction with 50 µg/ml of cycloheximide. Cells were then treated with or without TNF-α (10 ng/ml) and harvested after 15 minutes of stimulation. For EMSAs, epoxomicin (doses between 100 nM to 10 µM) were added to Hela cells in duplicate and subsequently treated with and without PMA (100 nM) for 1 hour of PMA stimulation before nuclear lysates were prepared as described in Mohan et al.; *J Biol. Chem.* 273, (1998) 25903–25914.

Example 1
Purification of Epoxomicin-Binding Proteins

We synthesized a biotinylated epoxomicin analog to serve as an affinity chromatography reagent. FIG. 1 shows the molecular structure of epoxomicin and epoxomicin-biotin. Epoxomicin-biotin was incubated with the murine thymoma cell line EIA for four hours, cell lysates were analyzed by SDS-PAGE and subsequently the membrane-immobilized cellular lysates were probed with streptavidin-HRP. A detailed procedure is given below.

10 L of EL4 cells ($10^6$ cells/ml) were harvested and resuspended in 50 ml of RPMI medium containing 10% PBS. Epoxomicin-biotin was added to final concentration of 8 µM and cells were incubated for 4 hours at 37° C. in 5% $CO_2$. After collection by centrifugation, cells were homogenized using a Powergen homogenizer in lysis buffer (25 mM HEPES, 5 mM EGTA, 50 mM NaF) plus protease inhibitors (10 µg/ml of leupeptin, pepstatin and soybean trypsin inhibitors and 1 mM PMSF). The high-speed (100,000×g) supernatant was loaded into a 1 ml streptavidin agarose to remove endogenous biotinylated proteins. The flow-through fraction was then incubated for 10 minutes with 50 ml of DE52 beads pre-equilibrated with lysis buffer, washed twice with 50 ml lysis buffer containing 0.1 M NaCl, and eluted with 50 ml lysis buffer containing 0.3 mM NaCl. SDS was added to the eluant at a final concentration of 0.5%, boiled for 10 minutes, and diluted 2.5× fold using lysis buffer. The diluted solution was loaded onto a 0.4 ml NeutrAvidin agarose column. The flow-through fraction was collected and reloaded onto the same column three times. After extensive washes, epoxomicin-biotin binding proteins were eluted by boiling the NeutrAvidin agarose in 0.4 ml ×SDS sample buffer. The purified protein complexes were separated by SDS-PAGE. Excised protein bands were identified by the W. M. Keck Foundation Biotechnology Resource Laboratory (Yale University) using LCQ (MS/MS) and automated Edman degradation of internal tryptic peptides.

Two major (23 and 30 kDa) and one minor (28 kDa) newly biotinylated bands were detected (FIG. 2, lane 1). These proteins were shown to specifically interact with epoxomicin-biotin since pretreatment of cells with a five-fold molar excess of epoxomicin prevents biotin binding to these proteins upon subsequent challenge with epoxomicin-biotin (FIG. 2, lane 2).

After large-scale purification of these epoxomicin-binding proteins using avidin affinity chromatography, the three epoxomicin-binding proteins were digested with trypsin and the resulting tryptic peptides subjected to MALDI-MS analysis. Comparison of these results with peptide masses generated from theoretical tryptic digests of putative open reading frames in GenBank revealed significant matches between two of the three epoxomicin binding proteins (23 and 28 kDa) and two murine proteasomal subunits.

The 23 kDa band was identified as LMP7, a γ-interferon-inducible catalytic β subunit of the 20S proteasome. The percentage of the LMP7 protein sequence covered was 31.9% for the tryptic peptides from the 23 kDa band. In some experiments, an additional 24 kDa band was observed. MALDI-MS analysis revealed that this band is also LMP-7. This minor LMP-7 band may represent a post-translational modification or possibly allelic variation.

MALDI-MS analysis of tryptic peptides from the 28 kDa band identified this epoxomicin-binding protein as the γ-interferon-inducible proteasome catalytic subunit, MECL1, with 29% coverage between the tryptic peptides and the MECL1 protein sequence. Although the tryptic peptide masses of the 30 kDa band matched 19.9% of the predicted protein sequence of the Z catalytic subunit of the proteasome, this was less than the 20% match criteria used to confirm protein identity. Therefore, automated Edman degradation was performed on an internal tryptic peptide from this 30 kDa protein. The resulting eleven amino acid sequence was identical to residues 185–195 of the murine Z β catalytic proteasome subunit. Thus, epoxomicin was shown to bind covalently the LMP7, MECL1, and Z proteasome catalytic subunits.

Given that epoxomicin binds both Z and its IFN-γ-inducible conterpart MECL1, we tested whether epoxomicin also binds in an analogous manner to the subunit X, which is the housekeeping part of LMP7. Epoxomicin-biotin binding to the human B cell line LCL 721.45 gave a similar pattern as observed with the murine lymphoma line EL4 (FIG. 2, lane 3). However, epoxomicin-biotin binding to a LCL 721.45 derivative line which does not express LMP7 or LMP2, resulted in two epoxomicin-biotin-binding proteins of 23 and 30 kDa (FIG. 2, lane 4). Immunoblot analysis confirmed that these bands are the X and Z proteasome subunits, respectively.

Example 2
Enzyme Kinetic Assays

Peptide-AMC (AMC is 7-aminomethyl coumarin) substrates (5 μM Suc-LLVY-AMC (SEQ ID NO:1), 5 μM Z-LLE-AMC, 5–10 μM Boc-LRR-AMC) and inhibitors in DMSO were added to 50 μL, of assay solutions (20 mM Tris-HCl; pH 8.0, 0.5 mM EDTA, plus 0.035% SDS for Suc-LLVY-AMC (SEQ ID NO:1) and Z-LLE-AMC assays). Bovine red blood cell proteasome was added to 50 μL of the assay buffer containing substrates and inhibitors for a final volume of 100 μL at room temperature (22–26°) in DynEx Microfluor 96-well plates and the fluorescence emission was immediately measured at 460 nm ($\lambda_{ex}$, 360 nm) using a Cytofluor fluorescence plate reader for 50 minutes. The $k_{obs}/[I]$ values were obtained using Kaleidagraph by non-linear least squares fit of the data to the following equation for slow and tight binding inhibition: Fluorescence=$v_s t$+ $[(v_O-v_s)/k_{obs}][1-e^{(-k\text{obs}'t)}]$, where $v_O$ and $v_s$ are the initial and final velocities, respectively and $k_{obs}$ is the reaction rate constant. Values of $k_{obs}$ represent an average of typically nine measurements (generally three independent experiments with three different inhibitor concentrations). Peptide epoxides exhibiting low or no inhibition at 150 μM were not tested at higher concentrations in order to avoid problems with low solubility. It is assumed that $k_{obs}/[I]$ values for these compounds are low compared with inhibitors that allow curve-tit to data collected at concentrations lower than 150 μM. Dilutions of bovine erythrocyte 20S proteasome (2.5 mg/ml) were as follows: 1:1200 dilution final for Suc-LLVY-AMC (SEQ ID NO:1) activity, 1:3000 for Z-LLE-AMC, 1:800 for Boc-LRR-AMC, Inhibition reactions were performed as previously described in Meng et al., Cancer Research, 59:2798–2801 (1999). For calpain inhibition assays, the enzyme was used at 1 unit/mL, and Suc-LLVY-AMC (SEQ ID NO:1) was used at a final concentration of 10 μM in assay containing 20 mM Tris, pH 8.0/1 mM CaCl$_{2/2}$ mM DTT. Cathepsin B was used as concentration of 0.005 unit/mL in 100 mM sodium acetate/5 mM EDTA, pH 5.5, and cathepsin substrate III was used is substrate at 40 μM. Kinetic assays were performed as described for the proteasome.

Example 3
Effect of Inhibitor Length on Proteasome Inhibition

We investigated the potency of inhibitors of various length. Mono-, di-, tri- and tetraleucine α',β'-epoxides were ranked by determination of the $k_{obs}/[I]$ values for inhibition of the chymotrypsin-like, trypsin-like, and PGPH activities of purified bovine erythrocyte 20S proteasome. Enzyme kinetic assays were performed as described in Example 2. The results are presented in Table 1.

TABLE 1

Proteasomal Inhibition by Peptide Epoxides of Varying Length

| | $k_{obs}/[I]$ (M$^{-1}$ s$^{-1}$) | | |
|---|---|---|---|
| | Chymotrypsin-like activity | trypsin-like activity | PGPH activity |
| | 14,000 (50–150 nm) | † | 9.2 (100–160 μM) |
| | 780 (1–2.5 μM) | 5.1 (100–150 μM) | 120 (8–12 μM) |

TABLE 1-continued

Proteasomal Inhibition by Peptide Epoxides of Varying Length

| | $k_{obs}/[I]\ (M^{-1}\ s^{-1})$ | | |
|---|---|---|---|
| | Chymotrypsin-like activity | trypsin-like activity | PGPH activity |
| 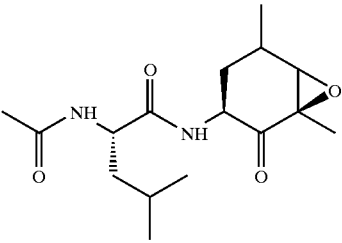 | 3.1 (100–160 μM) | † | † |
| 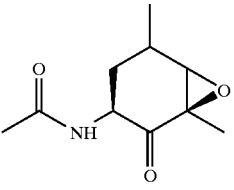 | † | † | † |

The dagger symbol indicates that inhibition at 150 μM was either absent or insufficient to allow curve-fit to the collected data. The tetrapeptide showed strong inhibition of the chymotrypsin-like activity and had essentially no effect on the trypsin-like and PGPH activities. The tripeptide showed significantly reduced inhibition of the chymotrypsin-like activity with a small increase in the inhibition of PGPH activity. The di- and monopeptides were found to be essentially inactive against all three proteasomal activities.

Example 4
Proteasome/Protease Inhibition Studies

Purified bovine erythrocyte proteasome was enzymatically assayed using a variety of different substrates and inhibitors. In order to evaluate the rates of proteolytic inactivation by inhibitors, $k_{association}$ ($k_{obs}/[I]$) values were determined using fluorogenic peptide substrates over a range of inhibitor concentrations. The results are shown in Table 2.

TABLE 2

Proteasomal Association Contants

| | $k_{assoc} = k_{obs}/[I]\ (M^{-1}s^{-1})$ | | |
|---|---|---|---|
| compound | Chymotrypsin-like activity | Trypsin-like activity | PGPH activity |
| epoxomicin | 35,400 ± 1400 (40–80 nM) | 287 ± 71 (6–10 μM) | 34 ± 4.8 (25–75 μM) |
| clasto-lactacystin β lactone | 8530 ± 280 (200–400 nM) | 253 ± 41 (6–10 μM) | 37 ± 4.7 (25–75 μM) |
| NLVS | 6790 ± 919 (200–400 nM) | 5.3 ± 2.8 (50–100 μM) | 6.4 ± 2.3 (50–100 μM) |

As shown in Table 2, epoxomicin most potently inhibited the chymotrypsin-like activity of the 20S proteasome with a $k_{assoc}$ value of 35,400 $M^{-1}s^{-1}$. This rate of inactivation is greater than four-and five-fold faster than clastolactacystin β-lactone and the vinyl sulfone NLVS, respectively. Interestingly, epoxomicin and clasto-lactacystin β-lactone displayed near identical inhibitory activities against the trypsin-like and the PGPH activities.

Example 5
Inhibition of PGPH Activity

As the first step toward developing a peptide inhibitor(s) selective for PGPH activity of the proteasome (that is, cleavage of peptide bonds after acidic residues), we synthesized a series of peptidyl (α'β'-epoxyketones with the acidic residue glutamate at a first amino acid position. Both isooctanoyl-Ser-Glu- and isooctanoyl-Thr-Glu-α',β'-epoxyketones proved to be poor PGPH-selective inhibitors (data not shown). This was surprising since eponemycin (isooctanoyl-Ser-Leu-α',β'-epoxyketone) shows a modest selectivity toward the PGPH activity (Table 1). Similarly, other compounds, such as Ac-Ile-Ile-Thr-Glu- (SEQ ID NO:3), Ac-Ala-Val-Glu-, Ac-Ile-Val-Glu-, Ac-Gly-Pro-Phe-Glu- (SEQ ID NO:4), and Ac-Pro-Phe-Glu-α',β'-epoxyketones, did not display any significant selectivity for the PGPH activity (data not shown).

TABLE 3

Enzyme Inhibition for 20S Proteasome Peptidase Activities

| | $k_{obs}/[I]\ (M^{-1}s^{-1})$ | | |
|---|---|---|---|
| Compounds | Chymotrypsin-like | PGPH | Trypsin-like |
| Ac-GPFL-Ex (SEQ ID NO:5) | 5 ± 1 (50–150 μM) | 190 ± 10 (4–215 μM) | N1 (100–150 μM) |
| Ac-NorLPFL-Ex (SEQ ID NO:6) | 1.9 ± 0.6 (100–150 μM) | 115 ± 15 (10–40 μM) | N1 (100–150 μM) |
| Ac-PFL-Ex | 42 ± 2 (50–100 μM) | 32 ± 6 (25–75 μM) | N1 (100–150 μM) |
| N-dimethylamino-benzoyl-PFL-EX | 220 ± 70 (1–2 μM) | 150 ± 40 (10–40 μM) | N1 (100–150 μM) |
| Isooctanioc-PFL-Ex | 190 ± 60 (1–2 μM) | 194 ± 4 (10–40 μM) | N1 (100–150 μM) |
| Benzoylbenzoic-PFL-Ex | 8.7 ± 0.2 (80–100 μM) | 140 ± 30 (10–40 μM) | N1 (100–150 μM) |

TABLE 3-continued

Enzyme Inhibition for 20S Proteasome Peptidase Activities

| Compounds | $k_{obs}/[I]\ (M^{-1}s^{-1})$ | | |
|---|---|---|---|
| | Chymotrypsin-like | PGPH | Trypsin-like |
| Pyrazinecarbonyl-PFL-Ex | 520 ± 40 (1–2 μM) | 23 ± 3 (40–80 μM) | 3.7 ± 1.1 (125–150 μM) |
| Ac-GGPFL-Ex (SEQ ID NO:7) | 170 ± 60 (20–60 μM) | 170 ± 30 (10–40 μM) | 1.3 ± 0.3 (125–150 μM) |
| Ac-PPFL-Ex (SEQ ID NO:8) | 6.4 ± 3.3 (20–60 μM) | 10.6 ± 0.3 (40–80 μM) | NI (125–150 μM) |
| N-acetyl-piperidinecarbonyl-PFL-Ex | 31.2 ± 0.6 (60–80 μM) | 45.3 ± 2.2 (40–80 μM) | NI (125–150 μM) |
| Ac-IVL-Ex | 5 ± 0.1 (100–150 μM) | 14.6 ± 4.2 (50–125 μM) | 6.7 ± 0.1 (100–150 μM) |
| Ac-AVL-Ex | 10.8 ± 0.2 (100–150 μM) | 12.7 ± 1.3 (50–100 μM) | 1.8 ± 0.1 (125–150 μM) |
| Eponemycin | 58 ± 14 (25–62.5 μM) | 175 ± 2 (12.5–50 μM) | 17 ± 3 (100–150 μM) |

The one-letter code for amino acids is used in Table 3. The values in parentheses indicate the concentration range of inhibitor used. The entry "NI" indicates no inhibition observed in the concentration range indicated. The prefix "Ac" is acetyl, the suffix "Ex" is α',β'-epoxide having an α'-methyl substituent, and "NorL" is nor-leucine. The stereochemistry of all epoxides is such that the oxygen atom is above the plane of the molecule when drawn as shown in formula I (that is, the β stereoisomer).

As seen in Table 3, the first two entries (Ac-GPFL-Ex (SEQ ID NO:5), and Ac-NorLPFL-Ex (SEQ ID NO:6)) showed the highest selectivity toward the PGPH activity with 35- and 60-fold higher values of $k_{obs}/[I]$ for inhibition of the PGPH activity than the chymotrypsin-like activity, respectively. In contrast, the compounds N-dimethylaminobenzoyl-PFL-EX and isooctanioc-PFL-Ex showed no selectivity by inhibiting both the chymotrypsin-like and the PGPH activities. Despite their differences in selectivity toward the PGPH activity, compounds Ac-GPFL-Ex (SEQ ID NO:5), Ac-NorLPFL-Ex (SEQ ID NO:6), N-dimethylaminobenzoyl-PFL-EX and isooctanioc-PFL-Ex showed similar values of $l_{obs}/[I]$ for inhibition of the PGPH activity, whereas all showed no inhibition of the trypsin-like activity of the proteasome Table 1 shows that α',β'-epoxyketone inhibitors with Pro-Phe-Leu at the P3-P1 positions displayed no significant, if any, inhibition of the trypsin-like activity, regardless of the nature of residues at the P4 position. These results suggest that the presence of Pro-Phe-Leu as the backbone of the proteasome inhibitor would prevent these inhibitors from binding the subunits responsible for the trypsin-like activity. Secondly, the presence of a protecting group consisting a bulky aromatic group in place of an acetyl group at the amino terminus provided a stronger inhibition (~5–2-fold) towards the chymotrypsin-like activity, thus making them far less PGPH-selective. Similarly, compounds with larger groups at the P4 position displayed a modest increase in inhibition of the chymotrypsin-like activity.

Example 6
Specificity for 20S Proteasome

We also investigated whether epoxomicin shared protease inhibitory specificities with two other classes of peptide-based proteasome inhibitors (i.e., peptide aldehydes and peptide vinyl sulfones). While several peptide aldehydes potently inhibit the proteasome, they also inhibit other intracellular non-proteasomal proteolytic activities such as calpain and lysosomal proteases (cathepsins). Epoxomicin did not display any inhibitory activity against the calcium-dependent protease calpain, papain, chymotrypsin, trypsin and cathepsin B at concentrations up to 50 μM, whereas, the vinyl sulfone NLVS and clasto-lactacystin β-lactone significantly inhibited cathepsin B enzymatic activity at 10 μM and 50 μM, respectively.

Figure 4:
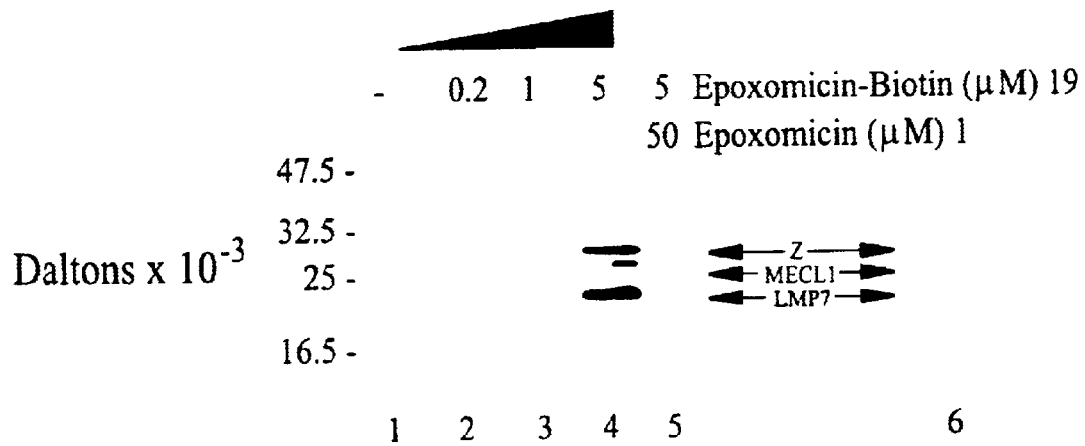
FIG. 4 is an electrophoretic gel of the concentration dependence of biotin-epoxomicin on protein binding.

Since biotin-epoxomicin was used to identify epoxomicin binding proteins, it was important to determine if the biotin affinity linker spuriously affects the binding specificity of the natural product. A possible change in subunit binding specificity is plausible since it has been shown that the length of peptide-based proteasome inhibitors influences their specificity for different proteasome catalytic subunits. For example, the vinyl sulfone peptide, NLVS, has been shown to bind to the X subunit and its γ-interferon-inducible counterpart LMP7, both of which are responsible for the CT-L proteolytic activity. However, an extension of the peptide backbone by an additional amino acid allows the resulting tetrapeptide vinyl sulfone, H-Leu-Leu-Leu-Leu-VS (SEQ ID NO:9) to bind LMP7/X subunits as well as the Z subunit and its γ-interferon-inducible counterpart, MECL1. The latter two subunits are responsible for the trypsin-like (T-L) catalytic activity of the proteasome. To exclude the possibility that biotinylation alters the binding of epoxomicin to its target proteins, we prepared [³H]-labeled epoxomicin, as shown in FIG. 3. The benzyl ester of fully protected tripeptide was removed by hydrogenolysis to furnish the acid, which was coupled to the right-hand fragment. The resulting Fmoc-protected epoxomicin was successively treated with piperidine, [³H]-acetic anhydride, and tetrabutylammonium fluoride to give [³H]-epoxomicin. Various concentrations of epoxomicin-biotin were added to different sets of murine thymoma EL4 cells for 6 hours. Cell lysates were analyzed by denaturing sodium dodecyl sulfate polyacrylamide gel electrophoresis (SDS-PAGE), followed by protein immobilization on PVDF membrane and visualization of biotlinylated proteins via avidin-horseradish peroxidase enhanced chemiluminescence. Since SDS denatures proteins, the presence of biotinylated proteins after addition of biotinylated epoxomicin and SDS-PAGE indicates the presence of covalent protein adduct formation. As shown in FIG. 4, the addition of increasing concentrations of biotinylated epoxomicin resulted in newly biotinylated proteins of 23 kDa and 30 kDa in size. In addition to these two major epoxomicin-binding proteins, a minor 28 kDa protein band was also observed. MALDI-MS analyses of peptides generated by trypsin digestion of 23, 30, and 28 kDa epoxomicin-binding proteins identified them as LMP2, Z and MECLI catalytic subunits, respectively. In addition, the use of different concentrations of epoxomicin-biotin demonstrated that LMP7 is more rapidly modified than the Z or MECL1 subunits. Adduct formation between epoxomicin-biotin and these binding proteins most likely occurs via nucleophilic attack on the epoxyketone of epoxomicin by the proteasome subunits' catalytic amino-terminal threonine. This has been previously shown for lactacystin binding. Incubation with a ten equivalent excess of epoxomicin with cells for 30 minutes prior to challenge with epoxomicin-biotin resulted in a significant decrease in biotin incorporation into all three protein targets (FIG. 4, lane 5). This competition for epoxomicin-biotin binding confirms that the interaction is specific.

As shown in FIG. 4, lane 6, addition of [³H] epoxomicin to purified murine spleen proteasome resulted in the same protein binding pattern observed with epoxomicin-biotin (FIG. 4, lane 4). This finding validates the use of epoxomicin-biotin as a probe of epoxomicin's biological activity.

Example 8
Effect of Epoxomicin on n53 Cell Levels

Given that epoxomicin covalently binds proteasome subunits in intact cells and inhibits the proteolytic activity of purified proteasome in vitro, we investigated the ability of epoxomicin to inhibit in vivo proteasome function in cultured cells. The tumor suppressor p53 is a known target of the proteasome.

Figure 5:
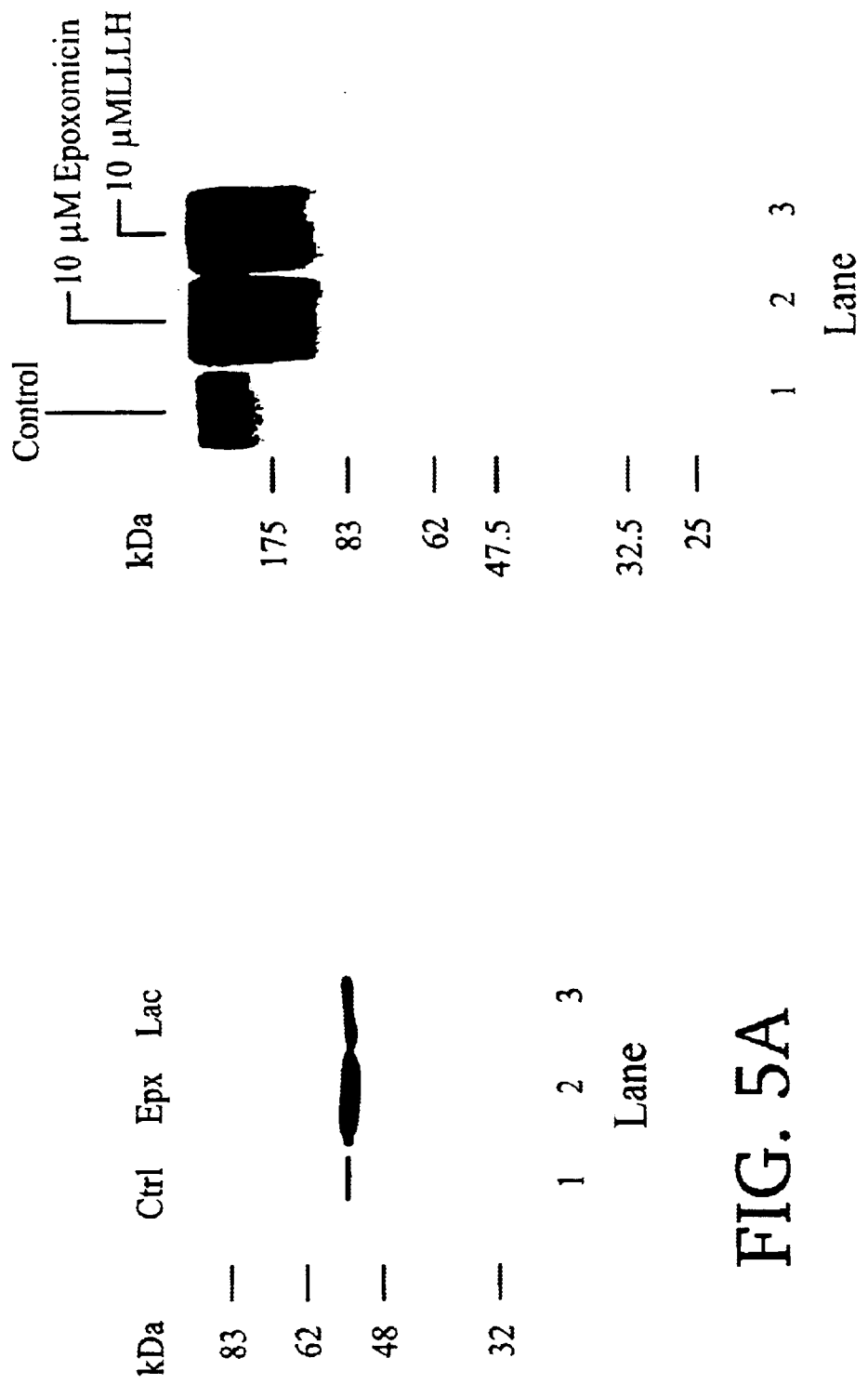
FIG. 5A is an α-p53 immunoblot analysis showing accumulation of p53 in epoxomicin-treated cells.
FIG. 5B is an α-ubiquitin immunoblot analysis showing accumulation of ubiquitinated proteins in epoxomicin-treated cells.

As shown in FIG. 5A, incubation of HUVECs with 100 nM epoxomicin (Epx) for 6 hours resulted in a 30-fold increase in p53 protein levels. In contrast, incubation with a 50-fold higher concentration (5 µM) of lactacystin (Lac) resulted in only a 10-fold increase of p53 levels over that of untreated cells. The control experiment (Crtl) was carried out with vehicle only. Since inhibition of proteasome function should result in increased levels of ubiquitinated proteins, we also analyzed the effect of epoxomicin on total intracellular ubiquitinated protein accumulation.

Incubation of Hela cells with 10 µM epoxomicin for 2 hours (FIG. 5B, lane 2) resulted in the accumulation of multiple higher molecular weight bands recognized by anti-ubiquitin antibody. These upper molecular weight bands were also observed in cellular lysates of cells treated with the peptide aldehyde inhibitor, Z-LLL-H (FIG. 5B, lane 3). The control experiment (Crtl) was carried out with vehicle only.

Example 9
Optimized Enzyme Inhibitors

Investigations of variation in the identities of amino acid sidechains were carried out to determine the effect of the sidechains on inhibition of proteasomal activities. The effect of steric bulk was investigated at each of the various positions of a tetrapeptide epoxide, with other side chains held constant as leucine.

The effect of steric bulk at $P_2$ was investigated with the following series of compounds, represented by the general structure below.

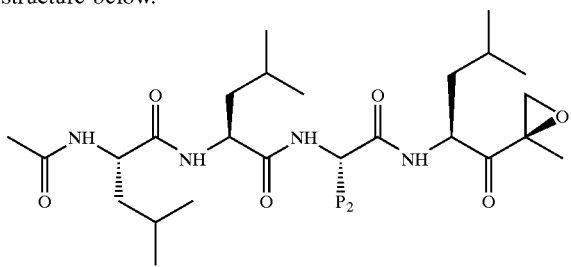

When $P_2$ was methyl, the $k_{obs}/[I]$ for chymotryptic-like activity using Suc-LLVY-AMC (SEQ ID NO:1) was 16,000, the $k_{obs}/[I]$ for tryptic-like activity using Boc-LRR-AMC was 4.1, and the $k_{obs}/[I]$ for PGPH activity using Z-LLE-AMC was 20.

When $P_2$ was isopropyl, the $k_{obs}/[I]$ for chymotryptic-like activity using Suc-LLVY-AMC (SEQ ID NO:1) was 14,000, the $k_{obs}/[I]$ for tryptic-like activity using Boc-LRR-AMC was not measurable, and the $k_{obs}/[I]$ for PGPH activity using Z-LLE-AMC was 9.2.

When $P_2$ was phenyl, the $k_{obs}/[I]$ for chymotryptic-like activity using Suc-LLVY-AMC (SEQ ID NO:1) was 54,000, the $k_{obs}/[I]$ for tryptic-like activity using Boc-LRR-AMC was not measurable, and the $k_{obs}/[]$ for PGPH activity using Z-LLE-AMC was not measurable.

When $P_2$ was 1-naphthyl, the $k_{obs}/[I]$ for chymotryptic-like activity using Suc-LLVY-AMC (SEQ ID NO:1) was 29,000, the $k_{obs}/[I]$ for tryptic-like activity using Boc-LRR-AMC was not measurable, and the $k_{obs}/[I]$ for PGPH activity using Z-LLE-AMC was not measurable.

The effect of steric bulk at $P_3$ was investigated with the following series of compounds, represented by the general structure below.

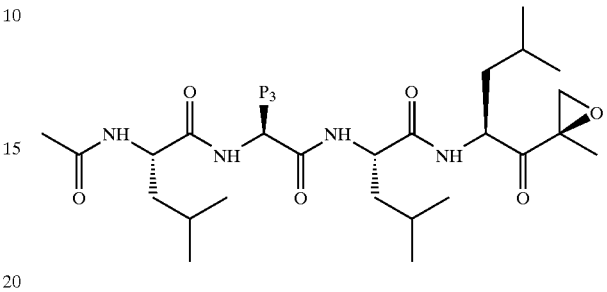

When $P_3$ was methyl, the $k_{obs}/[I]$ for chymotryptic-like activity using Suc-LLVY-AMC (SEQ ID NO:1) was 1,300, the $k_{obs}/[I]$ for tryptic-like activity using Boc-LRR-AMC was 2.0, and the $k_{obs}/[I]$ for PGPH activity using Z-LLE-AMC was 130.

When $P_3$ was isopropyl, the $k_{obs}/[I]$ or chymotryptic-like activity using Suc-LLVY-AMC (SEQ ID NO:1) was 14,000, the $k_{obs}/[I]$ for tryptic-like activity using Boc-LRR-AMC was not measurable, and the $k_{obs}/[I]$ for PGPH activity using Z-LLE-AMC was 9.2.

When $P_3$ was phenyl, the $k_{obs}/[I]$ for chymotryptic-like activity using Suc-LLVY-AMC (SEQ ID NO:1) was 8,500, the $k_{obs}/[I]$ for tryptic-like activity using Boc-LRR-AMC was not measurable, and the $k_{obs}/[I]$ for PGPH activity using Z-LLE-AMC was not measurable.

When $P_3$ was 1-naphthyl, the $k_{obs}/[I]$ for chymotryptic-like activity using Suc-LLVY-AMC (SEQ ID NO:1) was 31,000, the $k_{obs}/[I]$ for tryptic-like activity using Boc-LRR-AMC was not measurable, and the $k_{obs}/[I]$ for PGPH activity using Z-LLE-AMC was not measurable.

The effect of steric bulk at $P_4$ was investigated with the following series of compounds, represented by the general structure below.

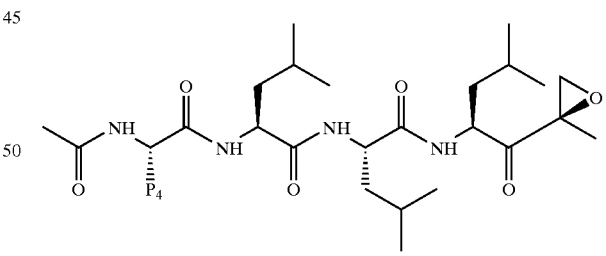

When $P_4$ was methyl, the $k_{obs}/[I]$ for chymotryptic-like activity using Suc-LLVY-AMC (SEQ ID NO:1) was 5,300, the $k_{obs}/[I]$ for tryptic-like activity using Boc-LRR-AMC was 3.8, and the $k_{obs}/[I]$ for PGPH activity using Z-LLE-AMC was 220.

When $P_4$ was isopropyl, the $k_{obs}/[I]$ for chymotryptic-like activity using Suc-LLVY-AMC (SEQ ID NO:1) was 14,000, the $k_{obs}/[I]$ for tryptic-like activity using Boc-LRR-AMC was not measurable, and the $k_{obs}/[I]$ for PGPH activity using Z-LLE-AMC was 9.2.

When $P_4$ was phenyl, the $k_{obs}/[I]$ for chymotryptic-like activity using Suc-LLVY-AMC (SEQ ID NO:1) was 37,000, the $k_{obs}/[I]$ for tryptic-like activity using Boc-LRR-AMC was 5.5, and the $k_{obs}/[I]$ for PGPH activity using Z-LLE-AMC was 78.

When $P_4$ was methylphenyl, the $k_{obs}/[I]$ for chymotryptic-like activity using Suc-LLVY-AMC (SEQ ID NO:1) was 63,000, the $k_{obs}/[I]$ for tryptic-like activity using Boc-LRR-AMC was 5.4, and the $k_{obs}/[I]$ for PGPH activity using Z-LLE-AMC was 50.

When $P_4$ was phenylmethyl, the $k_{obs}/[I]$ for chymotryptic-like activity using Suc-LLVY-AMC was 63,000, the $k_{obs}/[I]$ for tryptic-like activity using Boc-LRR-AMC was 5.4, and the $k_{obs}/[I]$ for PGPH activity using Z-LLE-AMC was 50.

When $P_4$ was 1-naphthyl, the $k_{obs}/[I]$ for chymotryptic-like activity using Suc-LLVY-AMC (SEQ ID NO:1) was 29,000, the $k_{obs}/[I]$ for tryptic-like activity using Boc-LRR-AMC was not measurable, and the $k_{obs}/[I]$ for PGPH activity using Z-LLE-AMC was not measurable.

When $P_4$ was p-benzoylphenyl, the $k_{obs}/[I]$ for chymotryptic-like activity using Suc-LLVY-AMC (SEQ ID NO:1) was 23,000, the $k_{obs}/[I]$ for tryptic-like activity using Boc-LRR-AMC was not measurable, and the $k_{obs}/[I]$ for PGPH activity using Z-LLE-AMC was not measurable.

Compounds with aromatic residues in positions $P_2$ and $P_3$ increased the inhibition of chymotrypsin-like activity, with phenylalanine ($P_2$) and 3-(1-naphthyl)alanine ($P_3$) as useful substituents. Small, neutral side chains in positions $P_2$ and $P_3$ can be used to make compounds showing inhibition of trypsin-like and PGPH activities, with alanine ($P_2$, $P_3$) as a useful substituent. Compounds with aromatic residues in position $P_4$ increased the inhibition of chymotrypsin-like activity, with phenylalanine and homophenylalanine as useful substituents. The same experiments carried out with bovine brain 20S proteasome resulted in similar rankings of substituents.

Example 10

A Particular Optimized Enzyme Inhibitor

A particular optimized inhibitor, referred to as "compound 16", was prepared and evaluated similarly. This compound had leucine at positions $P_1$ and $P_3$, phenylalanine at position $P_2$, and homophenylalanine at position $P_4$, as shown below.

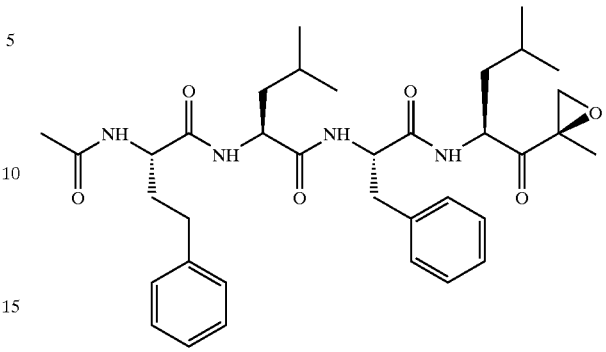

The $k_{obs}/[I]$ for chymotryptic-like activity using Suc-LLVY-AMC (SEQ ID NO:1) was 183,000. The $k_{obs}/[I]$ for tryptic-like activity using Boc-LRR-AMC was 7.1, and the $k_{obs}/[I]$ for PGPH activity using Z-LLE-AMC was 21.

The deacylated version of compound 16, is referred to as "compound 18", and was less potent a chymotrypsin-like inhibitor ($k_{obs}/[I]$ for Suc-LLVY-AMC (SEQ ID NO:1) of 5200), but also exhibited a major increase in potency for inhibition of trypsin-like activity ($k_{obs}/[I]$ for Boc-LRR-AMC of 580). Compound 18 was prepared directly from compound 16 by treatment with the N-terminal deprotecting agent, tetrabutylammoniumfluoride, in tetrahydrofuran.

Example 11

Comparison of Various Inhibitors of Proteasomal Activity

Efforts to optimize an inhibitor of CT-L activity in the proteasome lead to the development of peptide-based enzyme inhibitors having particular substituents in the P1–P4 positions. The results are presented in Table 4. In Table 4, compound 16 is the particular optimized enzyme inhibitor of Example 10. Compound 18 is the free amino terminal derivative of compound 16, also of Example 10.

TABLE 4

Proteasome Inhibition by Various Inhibitors

| | $k_{assoc} = k_{obs}/[I]$ (M$^{-1}$ s$^{-1}$) | | |
|---|---|---|---|
| compound | Chymotrypsin-like activity | Trypsin-like activity | PGPH activity |
| compound "16" | 166,000 (5–12 nM) | 7.1 (80–130 μM) | 21 (80–150 μM) |

TABLE 4-continued

Proteasome Inhibition by Various Inhibitors

| compound | $k_{assoc} = k_{obs}/[I]$ (M⁻¹ s⁻¹) | | |
| --- | --- | --- | --- |
| | Chymotrypsin-like activity | Trypsin-like activity | PGPH activity |
| compound "18" | 5200 (0.11 μM) | 580 (0.5–5 μM) | 11 (10–150 μM) |
| epoxomicin | 37,000 (30–80 nM) | 79 (8–12 μM) | 37 (50–100 μM) |
| PS-341 | 53,000 (30–100 nM) | 150 (5–35 μM) | 3200 (0.3–1 μM) |
| NLVS | 5000 (200–500 nM) | 3.4 (50–120 μM) | 4.0 (50–100 μM) |
| clasto-lactacystin β-lactone | 7400 (150–500 nM) | 68 (8–12 μM) | 47 (30–80 μM) |

Example 12
Correlation of Inhibition of Chymotrypsin-like Activity and Growth Inhibition of Bovine Aortic Endothelial Cells The in vitro data obtained with respect to inhibition of enzymatic, specifically chymotrypsin-like activity of 20S proteasome can be translated to in vivo applicability by correlating the inhibition with the inhibition of cell proliferation of bovine aortic endothelial (BAE) cells. BAE cells were cultured at 7% $CO_2$ and were grown in DMEM supplemented with 10% FBS, 1% penicillin/streptomycin (GIBCO), and 1 mM sodium pyruvate.

Approximately 1000 BAE cells were plated into each well of a 96-well culture plate. After an overnight incubation, different concentrations of proteasome inhibitors were added and incubation was continued for another five days. After five days, all inhibitors consistently inhibited cell growth in a dose-dependent manner. Subsequently, 74 kBq of [methyl-$^3$H]-thymidine was added to each well of the plate and the plate was incubated for another additional 4 hours. Cells were harvested using a Skatron Cell Harvester and incorporated radioactivity was quantified using liquid scintillation. Proliferation of BAE cells was assayed in triplicate in the presence of different concentrations of peptide epoxides. The results are shown in Table 5.

TABLE 5

Chymotrypsin-Like Activity Inhibition and BAE Cell Proliferation

| Inhibitor | $k_{assoc} = k_{obs}/[I]$ ($M^{-1}s^{-1}$) | $IC_{50}$ (nM) |
|---|---|---|
| Ac-LLAL-epoxide (SEQ ID NO:13) | 16,000 | 34 |
| Ac-LLFL-epoxide (SEQ ID NO:14) | 54,000 | 7 |
| Ac-LALL-epoxide (SEQ ID NO:15) | 1300 | 700 |
| Ac-LFLL-epoxide (SEQ ID NO:16) | 8500 | 16 |
| Ac-ALLL-epoxide (SEQ ID NO:17) | 5300 | 83 |
| Ac-hFLFL-epoxide (SEQ ID NO:18) | 166,000 | 20 |

The group "Ac" refers to an acetyl group as N-terminal protecting group, L is leucine, A is alanine, F is phenylalanine, and hF is homophenylalanine. "Epoxide" is the α'-methyl-α',β'-epoxide group as detailed herein.

Figure 6:
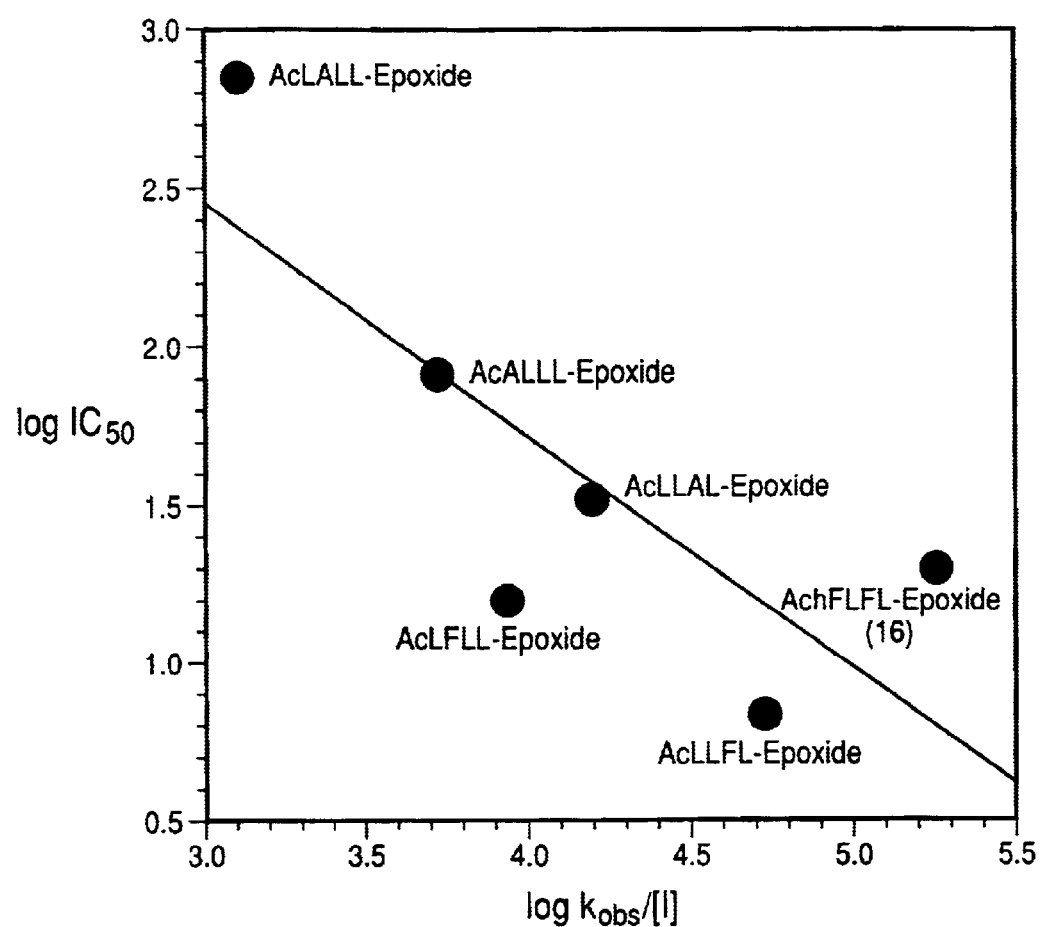
FIG. 6 is a plot of log $k_{obs}/[I]$ for inhibition of the chymotrypsin-like activity of 20S proteasome versus log $IC_{50}$ for inhibition of bovine aortic endothelial cell proliferation for particular enzyme inhibitors.

FIG. 6 shows the correlation of the log $k_{obs}/[I]$ values for inhibition of the chymotrypsin-like activity of 20S proteasome with the log $IC_{50}$ values for inhibition of bovine aortic endothelial cell proliferation by peptide epoxides. The trend observed in FIG. 6 suggests that the proteasome is the biological target for peptide epoxide compounds.

Example 13
Correlation of Inhibition of PGPH Activity and Growth Inhibition of Bovine Aortic Endothelial Cells Perturbation of the proteasome activity can result in inhibition of cell growth, and can further lead to cell death at elevated concentration of the proteasome inhibitors. This provides an excellent cell-based assay to assess the importance of each catalytic activity of the 20S proteasome in degradation of proteins involved in cell growth. We measured inhibition of proliferation of bovine aortic endothelial (BAE) cells with our α',β'-epoxyketone-based inhibitors with varying degree of specificity for the PGPH activity. When BAE cells were treated with Ac-GPFL-Ex (SEQ ID NO:5), Ac-NorLPFL-Ex (SEQ ID NO:6), N-dimethylaminobenzoyl-PFL-EX and isooctanioc-PFL-Ex, the compounds with the higher values of kobs/[I] for the inhibition of the chymotrypsin-like activity proved to be more active as antiproliferative agents (Table 6).

TABLE 6

PGPH Activity Inhibition and BAE Cell Proliferation

| Inhibitor | $IC_{50}$ ($\mu$M) |
|---|---|
| Ac-GPFL-epoxide (SEQ ID NO:5) | 58 |
| Ac-NorLPFL-epoxide (SEQ ID NO:6) | 53 |
| N-dimethylaminobenzoyl-PFL-epoxide | 0.4 |
| Isooctanoic-PFL-epoxide | 0.6 |
| Pyrazinecarbonyl-PFL-epoxide | 0.4 |

While all compounds arrested cell growth, a greater than 100-fold higher concentration of Ac-GPFL-Ex (SEQ ID NO5) and Ac-NorLPFL-Ex (SEQ ID NO:6) in comparison to N-dimethlylaminobenzoyl-PFL-EX and isooctanioc-PFL-Ex was needed to cause 50%-inhibition of proliferation. This result reflects that despite all these compounds have similar potency for inhibition of the PGPH activity, N-dimethylaminobenzoyl-PFL-EX and isooctanioc-PFL-Ex inhibit the chymotrypsin-like activity ~40–115-fold more strongly than Ac-GPFL-Ex (SEQ ID NO:5) and Ac-NorLPFL-Ex (SEQ ID NO:6) (see Table 6 above). Therefore, the greater than 100-fold difference in $IC_{50}$ values suggests that inhibition of PGPH activity of the proteasome in the cell is not sufficient to cause inhibition of proliferation of BAE cells.

Example 14
Electrophoretic Mobility Shift Assays

EMSAs were performed as described in Mohan et al.; *J. Biol. Chem.* 273, (1998) 25903–25914. In brief, consensus DNA binding oligonucleotide sequences for transcription factors NF-κB (5'-AGTTGAGGGGACTTTCCCAGGC-3'; SEQ ID NO:10) and AP-2 (5'-GATCGAAC TGACCGCCCGCGGCCCGT-3'; SEQ ID NO:11) from Santa Cruz Biotechnology were labeled with $^{32}$P-γ-ATP and incubated with equal amounts of nuclear lysates. Protein-DNA complexes were separated on 4% polyacrylamide gels under non-denaturing and non-reducing conditions. The gels were dried and exposed to a phosphoimaging screen (Molecular Dynamics) for quantitation of radioactivity in retarded bands. Results were representative of experiments performed at least twice.

Figure 7:
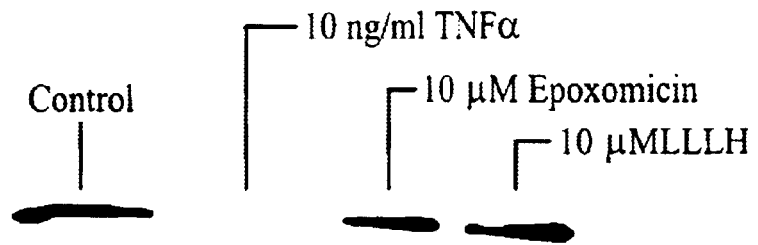
FIG. 7 is an electrophoretic gel Western blot analysis showing epoxomicin inhibition of activation of NF-αB.

We investigated whether epoxomicin blocks TNF-α-induced activation of NF-κB by stabilizing IκBα. Western blot analysis revealed that 10 ng/m)l TNF-α potently induced the degradation of 1-α in Hela cells within 15 minutes of treatment (FIG. 7. lane 2). However, pretreatment with 10 $\mu$M epoxomicin for 2 hours in the presence of cycloheximide inhibited IκBα degradation by 10 fold (FIG. 7, lane 3), to a level similar to that produced by treating TNF-α-stimulated cells with 10 $\mu$M of the peptide aldehyde inhibitor Z-LLLH (SEQ ID NO:12) (FIG. 7, lane 4). Control experiments with performed with vehicle (lane 1) and 10 ng/mL TNFα.

Next, using electrophoretic mobility shift assays (EMSA), we tested whether epoxomicin inhibits NF-κB DNA binding activity. Hela cells were treated with increasing concentrations of epoxomicin for 2 hours, and subsequently, 10 ng/mL TNF-α was added to drug-treated cells or to untreated cultures and incubated for one hour. Equal amounts of protein from nuclear extracts prepared from untreated and treated cultures were incubated with a radiolabeled NF-κB oligonucleotide or an control AP-2 oligonucleotide and fractionated on 4% polyacrylamide gels. Dried gels were exposed to a PhosphorImaging screen. The amount of radioactivity in the transcription factor-retarded bands was quantitated and represented as fold-change over that of untreated samples.

Figure 8:
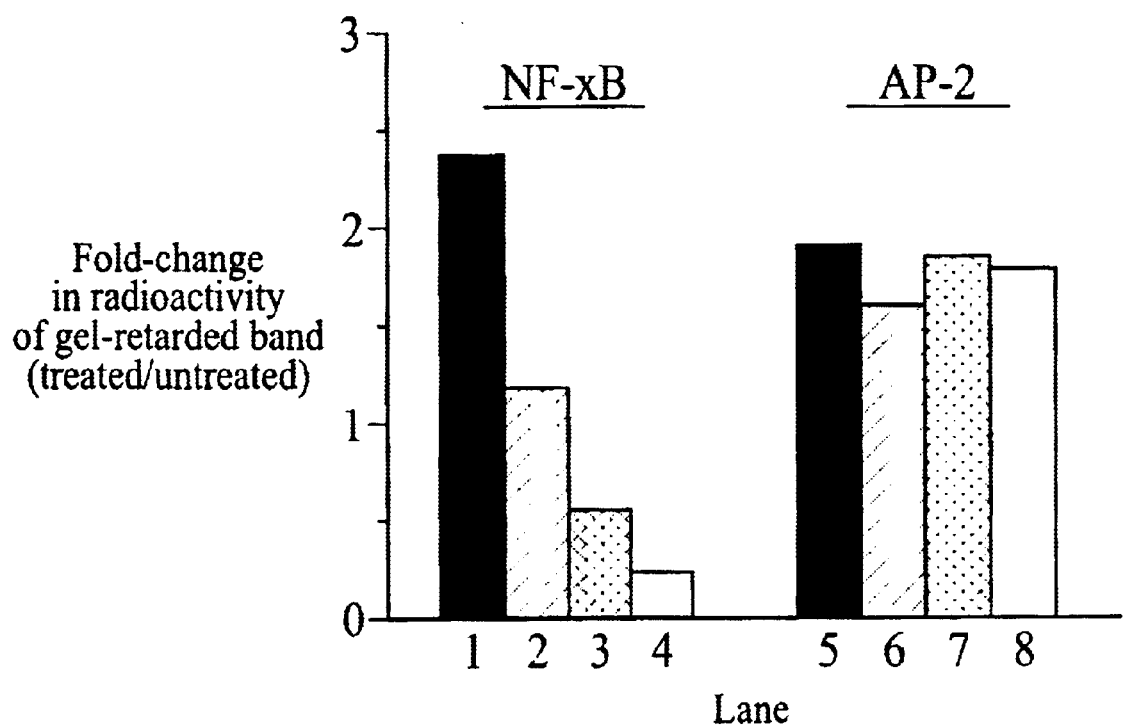
FIG. 8 is a plot of dose-dependence of epoxomicin on fold-change in radioactivity of gel-retarded bands, according to EMSA analysis.

EMSA of nuclear lysates derived from Hela cell cultures treated with TNF-α alone (FIG. 8, lanes 1 and 5) showed greater than 2-fold induction of NF-κB DNA binding activity over that of untreated cells. Epoxomicin pretreatment for 1 hour produced a significant dose-dependent reduction in TNF-α-stimulated NF-κB DNA binding activity (FIG. 8: 100 nM epoxomicin, lanes 2 and 6; 1 μM epoxomicin, lanes 3 and 7; 10 μM epoxomicin, lanes 4 and 8). These effects were selective, since we determined that the DNA binding activity of AP-2 was unaltered. Additionally, incubation of HEK 293 cells with 100 nM epoxomicin for up to 5 hours did not inhibit the PMA-stimulated DNA binding of transcription factor AP-2.

Epoxomicin targets NF-κB-mediated signaling, as shown by the fact that the natural product stabilized levels of BA resulting in inhibition of the DNS binding activity of NF-κB in the nucleus. This transcriptional inhibition is specific since DNA binding activity of activator protein-2 (AP-2), which was also stimulated by TNF-α and PMA, was not affected by epoxomicin up to 10 μM.

Example 15
Assay for Contact Sensitivity

In order to address the role of the proteasome in pathological inflammatory processes, we explored epoxomicin's potential as an in vivo anti-inflammatory agent. Contact sensitivity (CS) is a cutaneous immune inflammatory response that is mediated by CD4$^+$ T-cells in the classical delayed-type hypersensitivity (DTH) reaction. The DTH response in mice immunized with such haptens as picrylchloride (2,4,6-trinitro chlorobenzene), 2,4-dinitrofluorobenzene (DNFB), or 2,4,6-trinitrobenzene sulfone has been well characterized, being mediated by the proinflammatory cytokines γ-IFN and TNF-α. The DTH response, which is initiated by antigen-specific and nonspecific factors leads to local increase in vascular permeability, in part, by serotonin release that enables circulating CD4$^+$ effector T-cells to migrate into local sites of antigen challenge. Using the picrylchloride model of CS, we demonstrated that epoxomicin administration at non-toxic doses (as judged by absence of weight loss) was found to reduce CS significantly. Since picrylchloride also exerts a degree of non-specific irritation and nonspecific inflammation, we tested the efficacy of epoxomicin in the skin irritation assay using nonimmunized mice. A single bolus of epoxomicin abrogated 95% of the inflammatory response.

Contact sensitivity (CS) and irritant response assays to picrylchloride challenge was performed essentially as described in Tsuji et al. *J. Immunol.*, 156, (1996) 4444–50, with slight modifications. In brief, mice were injected intraperitoneally (i.p.) daily for six days with vehicle or epoxomicin (0.58 mg/kg body weight) solubilized in 10% DMSO-phosphate buffered saline. Six days after immunization with picrylchloride. car thickness measurements (0 hour) of both ears were made in triplicate with an engineer's micrometer (Peacock dial thickness gauge, Ozaki Manufacturing Co., LTD., Japan). Mice were subsequently challenged on both ear lobes by application of 10–15 microliters of a 0.2–0.8% solution of picryichloride or DNFB (solubilized in acetone/ high-grade extra virgin olive oil). Ear swelling measurements were made again 24 hours post-ear challenge. In a second assay. elicitation of inflammatory response to the nonspecific vascular activation and permeability effects of irritant response were determined using two groups of four non-immunized mice. The 0-hour ear thickness measurements were made, a single high-dose injection of epoxomicin (2.9 mg/kg) was delivered intraperiteoneally to one group and the control group was treated with vehicle. After one hour, the cars of all mice were challenged with irritant as in CS assay and ear thickness measurements taken 24 hours post-ear challenge.

Figure 9:
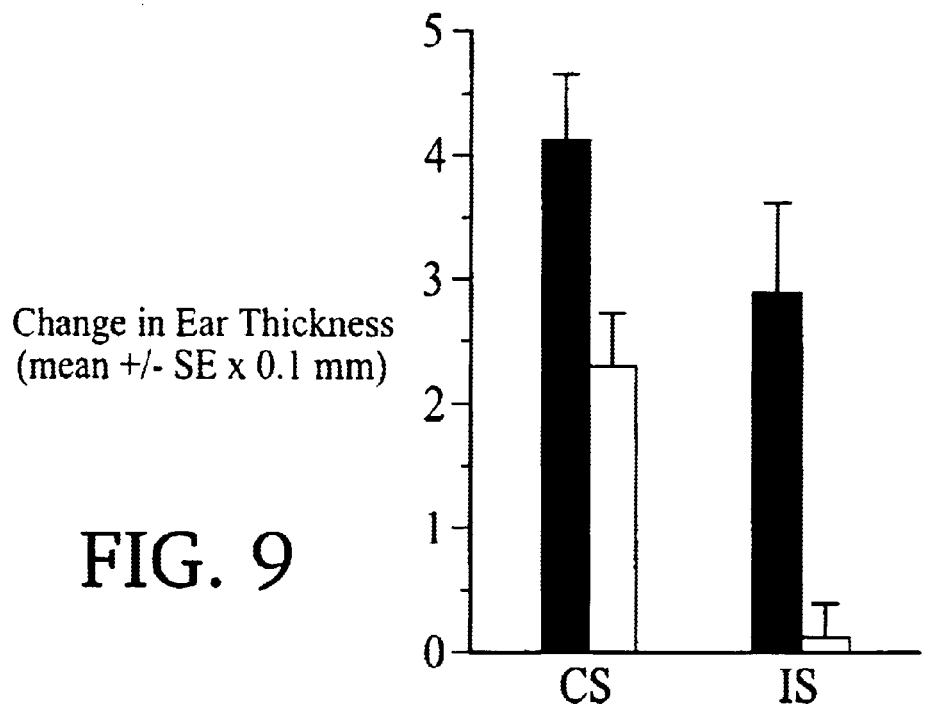
FIG. 9 is a plot of ear-swelling responses for contact sensitivity and irritant sensitivity according to picrylchloride challenges.

Contact sensitivity is an inflammatory response to certain classes of chemical compounds and haptens. Based on inhibition of NF-κB activation in cell culture, described in Example 14, we hypothesized that epoxomicin would have anti-inflammatory activity in vivo. To test this hypothesis, epoxomicin was evaluated in the picrylchloride mouse model of contact sensitivity. Mice were immunized with picrylchloride and 6 days post-immunization were challenged by application of picrylchloride on their ears. Ear thickness measurements were made at 0 and 24 hours after picrylchloride ear-challenge. As shown in FIG. 9A, daily treatment with epoxomicin at a non-toxic dose of 0.58 mg/kg/day reduced the contact sensitivity response by 44% relative to the control group of mice treated with vehicle alone.

Since the hapten can elicit a non-specific irritation-related inflammatory response, we explored the effects of epoxomicin on skin irritation-mediated inflammation using non-immunized mice. In a second experiment, mice were pretreated with epoxomicin at a dose 5 times higher than that used previously to test the idea that a single injection of the drug could reduce inflammation in response to picrylchloride ear challenge. Epoxomicin administered at 2.9 mg/kg potently inhibited the irritant-associated inflammatory response by 95% when ear edema measurements were made 24-hour post challenge (FIG. 9B).

Figure 10:
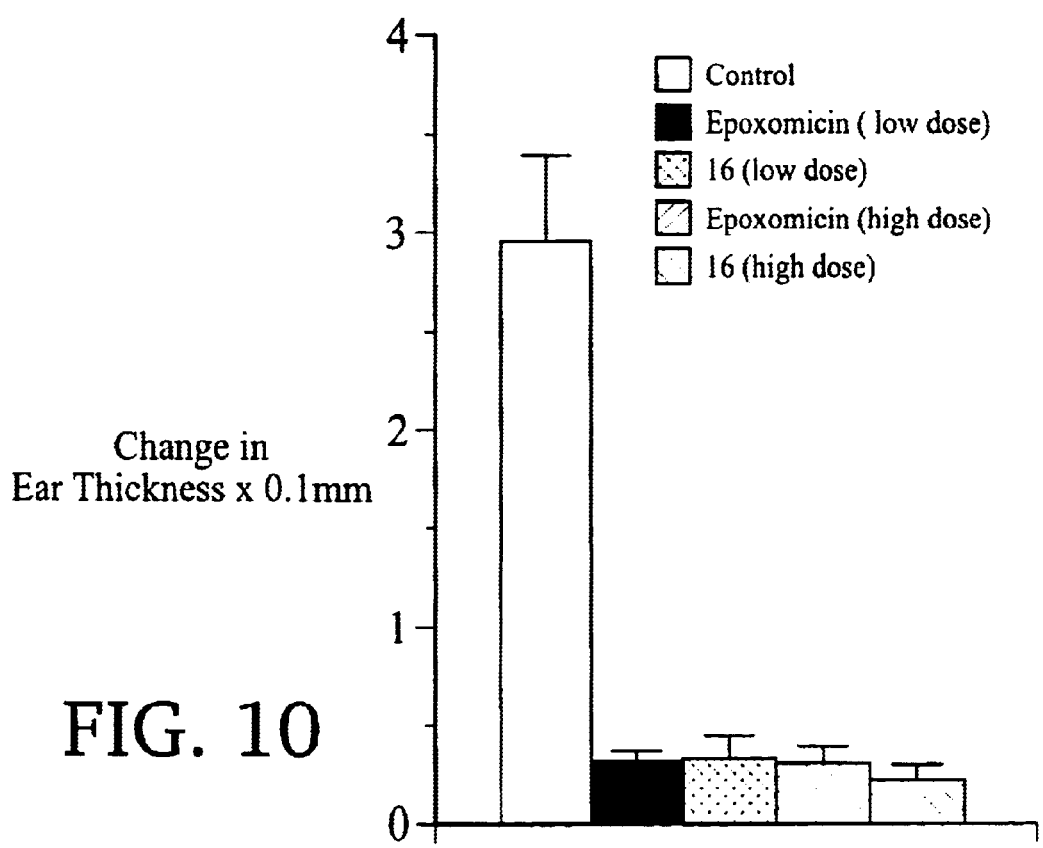
FIG. 10 is a plot of irritant sensitivity response (change in mouse ear thickness) for various dosages of epoxomicin and a particular anti-inflammatory compound.

Mice were injected with either a low dose (0.32 mg/kg) or a high dose (2.0 mg/kg) of epoxomicin, the inhibitor compound 16 (see Example 10) or vehicle (10% DMSO) alone, one hour before applying DNFB to the ear. The low dose corresponds to 0.58 μmol/kg and the high dose to 3.6 μmol/kg for both epoxomicin and compound 16. Ear thickness was measured at 0 and 24 hours after DNFB application. As shown in FIG. 10, a single dose of epoxomicin at 2.0 mg/kg inhibited ear inflammation by nine-fold over that of vehicle-treated controls. Interestingly, a six-fold lower amount of epoxomicin decreased inflammation by this same margin. A low dose of optimized inhibitor (compound 16) also exerted potent anti-inflammatory activity, reducing ear swelling by the same amount as epoxomicin. At the higher doses compound 16 decreased ear swelling by 12-fold, demonstrating a small increase, but an overall higher level of potency compared to epoxomicin.

For this class of inhibitors, strong in vitro enzyme inhibition correlates with strong in vivo activity, as illustrated by the cell anti-proliferative data of Example 12, and the anti-inflammatory data of Example 15.

Other Embodiments

It is to be understood that while the invention has been described in conjunction with the detailed description thereof, the forgoing description is intended to illustrate and not limit the scope of the invention, which is defined by the scope of the appended claims. Other aspects, advantages, and modifications are within the scope of the following claims.

What is claimed is:

1. A compound having a structure that conforms to structure I:

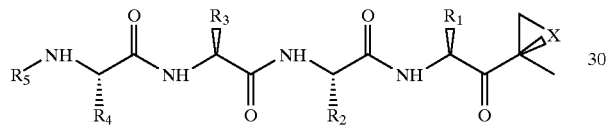

X is a heteroatom;

$R_1$, $R_2$, $R_3$, and $R_4$ are, independently, hydrogen or a branched or unbranched: $C_{1-6}$ alkyl group, $C_{1-4}$ hydroxy alkyl group, $C_{1-6}$ alkoxy, or aryl or aryl-substituted $C_{1-6}$ alkyl group, any of which can be substituted with amide linkages, amines, carboxylic acids and salts thereof, carboxyl esters, thiols, or thioethers; and $R_5$ is a chain of amino acids, hydrogen, an acetyl group, or a protecting group, with the proviso that, simultaneously, $R_1$ is not iso-butyl, $R_2$ is not 1-hydroxy ethyl, $R_3$ is not sec-butyl, $R_4$ is not sec-butyl, and $R_5$ is not an acetyl group.

2. The compound of claim 1, wherein the compound inhibits a chymotrypsin-like activity, a trypsin-like activity, or a peptidyglutamyl peptide hydrolyzing (PGPH) activity of a 20S proteasome.

3. The compound of claim 2, wherein the compound, when present at concentrations below 5 μM, inhibits a chymotrypsin-like activity of the 20S proteasome but does not inhibit the trypsin-like activity or the PGPH activity of the 20S proteasome.

4. The compound of claim 2, wherein the compound, when present at concentrations below 50 μM, inhibits PGPH activity of the 20S proteasome but does not inhibit chymotrypsin-like or trypsin-like activity of the 20S proteasome.

5. The compound of claim 1, wherein the compound is a peptide α',β'-epoxy ketone or α',β'-aziridine ketone.

6. The compound of claim 1, wherein $R_1$, $R_2$, $R_3$, or $R_4$ are, independently, isobutyl, 1-naphthyl, phenylmethyl, or 2-phenylethyl.

7. The compound of claim 6, wherein $R_1$ is isobutyl.

8. A method of making a peptide α',β'-epoxy ketone or α',β'-aziridine ketone, the method comprising:

a) synthesizing a first molecule by (i) acetylating the amino terminal of a tripeptide to make an acetylated tripeptide; and (ii) catalytically hydrogenating the acetylated tripeptide to make the first molecule;

b) synthesizing a second molecule by (i) alkenylating a Weinreb amide of an amino acid having an amino terminal protection group to form an α',β'-unsaturated ketone; (ii) forming a three-membered ring containing a heteroatom at the α',β'-unsaturation side to form an α',β'-epoxy ketone or an α',β'-aziridine ketone; and (iii) removing the amino terminal protection group to form the second molecule; and c) coupling the first and second molecules to make a peptide α',β'-epoxy ketone or α',β'-aziridine ketone.

9. The method of claim 8, wherein the tripeptide has at least one hydroxy side chain, the method further comprising protecting the hydroxy side chain to make a protected hydroxy side chain-containing tripeptide; and deprotecting the hydroxy side chain after the coupling.

10. A pharmaceutical composition comprising:
a pharmaceutically effective amount of the compound of claim 1, wherein the compound ameliorates the effects of Alzheimer's disease, a muscle-wasting disease, cancer, a chronic infectious disease, fever, muscle disuse, denervation, nerve injury, or wasting, and
a pharmaceutically acceptable carrier.

11. An anti-inflammatory composition comprising the compound of claim 1 in an amount effective to inhibit inflammation in a patient to whom the composition is administered.

12. The anti-inflammatory composition of claim 11, wherein the compound is a peptide α',β'-epoxy ketone or α',β'-aziridine ketone.

13. The anti-inflammatory composition of claim 11, wherein $R_1$, $R_2$, $R_3$, and $R_4$ are, independently, branched or unbranched $C_{1-6}$ alkyl, $C_{1-6}$ hydroxy alkyl, $C_{1-6}$ alkoxy alkyl, aryl, or aryl-substituted $C_{1-6}$ alkyl.

14. The compound of claim 1, wherein the compound, when present at concentrations below 50 μM, inhibits the chymotrypsin-like activity, the trypsin-like activity, or the PGPH activity of an N-terminal hydrolase enzyme, but does not inhibit catalytic activity of non-proteasomal proteases.

15. A compound having the structure:

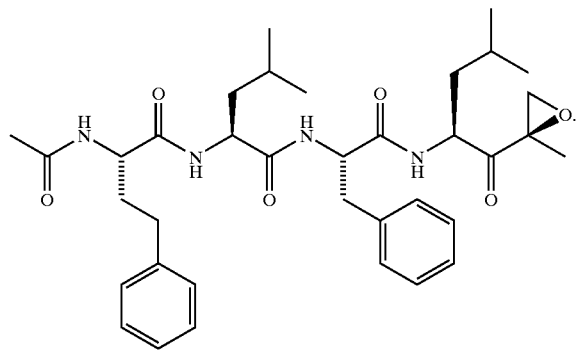

16. A compound of claim 1, wherein
X is O;
$R_1$, $R_3$, and $R_4$ are iso-butyl;
$R_2$ is selected from methyl, iso-propyl, phenyl, and 1-naphthyl; and
$R_5$ is acetyl.

17. A compound of claim 1, wherein
X is O;
$R_1$, $R_2$, and $R_4$ are iso-butyl;
$R_3$ is selected from methyl, iso-propyl, phenyl, and 1-naphthyl; and
$R_5$ is acetyl.

18. A compound of claim 1, wherein
X is O;
$R_1$, $R_2$, and $R_3$ are iso-butyl;
$R_4$ is selected from methyl, iso-propyl, phenyl, phenylmethyl, 1-naphthyl, and p-benzoylphenyl; and
$R_5$ is acetyl.

19. A compound of claim 1, wherein $R_2$ is a $C_{1-6}$ hydroxy alkyl group.

20. A compound of claim 1, wherein $R_4$ is a $C_{1-6}$ hydroxy alkyl group.

21. A compound of claim 19, wherein $R_4$ is a $C_{1-6}$ hydroxy alkyl group.

* * * * *

UNITED STATES PATENT AND TRADEMARK OFFICE
CERTIFICATE OF CORRECTION

PATENT NO.    : 6,831,099 B1
DATED         : December 14, 2004
INVENTOR(S)   : Crews et al.

It is certified that error appears in the above-identified patent and that said Letters Patent is hereby corrected as shown below:

Column 49,
Line 37, should be -- $C_{1-6}$ --, instead of "$C_{1-4}$"

Signed and Sealed this

Twenty-fourth Day of May, 2005

JON W. DUDAS
*Director of the United States Patent and Trademark Office*

SEQUENCE LISTING

<160> NUMBER OF SEQ ID NOS: 19

<210> SEQ ID NO 1
<211> LENGTH: 4
<212> TYPE: PRT
<213> ORGANISM: Artificial Sequence
<220> FEATURE:
<223> OTHER INFORMATION: Synthetically generated peptide
<221> NAME/KEY: MOD_RES
<222> LOCATION: 4
<223> OTHER INFORMATION: Xaa = Tyr-AMC ("AMC" is 7-aminomethyl coumarin)

<400> SEQUENCE: 1

Leu Leu Val Xaa
 1

<210> SEQ ID NO 2
<211> LENGTH: 10
<212> TYPE: PRT
<213> ORGANISM: Artificial Sequence
<220> FEATURE:
<223> OTHER INFORMATION: Synthetically generated peptide
<221> NAME/KEY: VARIANT
<222> LOCATION: 1, 6
<223> OTHER INFORMATION: Xaa = any amino acid

<400> SEQUENCE: 2

Xaa Gln Asn Pro Met Xaa Thr Gly Thr Ser
 1               5                  10

<210> SEQ ID NO 3
<211> LENGTH: 4
<212> TYPE: PRT
<213> ORGANISM: Artificial Sequence
<220> FEATURE:
<223> OTHER INFORMATION: Synthetically generated peptide
<221> NAME/KEY: MOD_RES
<222> LOCATION: 1
<223> OTHER INFORMATION: Xaa = Ac-Ile ("Ac" is an acetyl group)

<400> SEQUENCE: 3

Xaa Ile Thr Glu
 1

<210> SEQ ID NO 4
<211> LENGTH: 4
<212> TYPE: PRT
<213> ORGANISM: Artificial Sequence
<220> FEATURE:
<223> OTHER INFORMATION: Synthetically generated peptide
<221> NAME/KEY: MOD_RES
<222> LOCATION: 1
<223> OTHER INFORMATION: Xaa = Ac-Gly ("Ac" is an acetyl group)

<400> SEQUENCE: 4

Xaa Pro Phe Glu
 1

<210> SEQ ID NO 5
<211> LENGTH: 4
<212> TYPE: PRT
<213> ORGANISM: Artificial Sequence
<220> FEATURE:
<223> OTHER INFORMATION: Synthetically generated peptide
<221> NAME/KEY: MOD_RES
<222> LOCATION: 1
<223> OTHER INFORMATION: Xaa = Ac-Gly ("Ac" is an acetyl group)
<221> NAME/KEY: MOD_RES

```
<222> LOCATION: 4
<223> OTHER INFORMATION: Xaa = Leu-Ex ("Ex" is alpha, beta-epoxide
      having an alpha-methyl substituent)

<400> SEQUENCE: 5

Xaa Pro Phe Xaa
 1

<210> SEQ ID NO 6
<211> LENGTH: 4
<212> TYPE: PRT
<213> ORGANISM: Artificial Sequence
<220> FEATURE:
<223> OTHER INFORMATION: Synthetically generated peptide
<221> NAME/KEY: MOD_RES
<222> LOCATION: 1
<223> OTHER INFORMATION: Xaa = Ac-NorLeu ("Ac" is an acetyl group and
      "NorLeu" is nor-leucine)
<221> NAME/KEY: MOD_RES
<222> LOCATION: 4
<223> OTHER INFORMATION: Xaa = Leu-Ex ("Ex" is alpha, beta-epoxide
      having an alpha-methyl substituent)

<400> SEQUENCE: 6

Xaa Pro Phe Xaa
 1

<210> SEQ ID NO 7
<211> LENGTH: 5
<212> TYPE: PRT
<213> ORGANISM: Artificial Sequence
<220> FEATURE:
<223> OTHER INFORMATION: Synthetically generated peptide
<221> NAME/KEY: MOD_RES
<222> LOCATION: 1
<223> OTHER INFORMATION: Xaa = Ac-Gly ("Ac" is an acetyl group)
<221> NAME/KEY: MOD_RES
<222> LOCATION: 5
<223> OTHER INFORMATION: Xaa = Leu-Ex ("Ex" is alpha, beta-epoxide
      having an alpha-methyl substituent)

<400> SEQUENCE: 7

Xaa Gly Pro Phe Xaa
 1               5

<210> SEQ ID NO 8
<211> LENGTH: 4
<212> TYPE: PRT
<213> ORGANISM: Artificial Sequence
<220> FEATURE:
<223> OTHER INFORMATION: Synthetically generated peptide
<221> NAME/KEY: MOD_RES
<222> LOCATION: 1
<223> OTHER INFORMATION: Xaa = Ac-Pro ("Ac" is an acetyl group)
<221> NAME/KEY: MOD_RES
<222> LOCATION: 4
<223> OTHER INFORMATION: Xaa = Leu-Ex ("Ex" is alpha, beta-epoxide
      having an alpha-methyl substituent)

<400> SEQUENCE: 8

Xaa Pro Phe Xaa
 1

<210> SEQ ID NO 9
<211> LENGTH: 4
<212> TYPE: PRT
<213> ORGANISM: Artificial Sequence
<220> FEATURE:
<223> OTHER INFORMATION: Synthetically generated peptide
<221> NAME/KEY: MOD_RES
<222> LOCATION: 1
```

```
<223> OTHER INFORMATION: Xaa = H-Leu ("H" is hydrogen)
<221> NAME/KEY: MOD_RES
<222> LOCATION: 4
<223> OTHER INFORMATION: Xaa = Leu-VS ("VS" is vinyl sulfone)

<400> SEQUENCE: 9

Xaa Leu Leu Xaa
 1

<210> SEQ ID NO 10
<211> LENGTH: 22
<212> TYPE: DNA
<213> ORGANISM: Artificial Sequence
<220> FEATURE:
<223> OTHER INFORMATION: Consensus binding oligonucleotide

<400> SEQUENCE: 10
agttgagggg actttcccag gc                                              22

<210> SEQ ID NO 11
<211> LENGTH: 26
<212> TYPE: DNA
<213> ORGANISM: Artificial Sequence
<220> FEATURE:
<223> OTHER INFORMATION: Consensus binding oligonucleotide

<400> SEQUENCE: 11
gatcgaactg accgcccgcg gcccgt                                          26

<210> SEQ ID NO 12
<211> LENGTH: 4
<212> TYPE: PRT
<213> ORGANISM: Artificial Sequence
<220> FEATURE:
<223> OTHER INFORMATION: Synthetically generated peptide
<221> NAME/KEY: MOD_RES
<222> LOCATION: 1
<223> OTHER INFORMATION: Xaa =Z-Leu ("Z" is carbobenzyloxy)

<400> SEQUENCE: 12

Xaa Leu Leu His
 1

<210> SEQ ID NO 13
<211> LENGTH: 4
<212> TYPE: PRT
<213> ORGANISM: Artificial Sequence
<220> FEATURE:
<223> OTHER INFORMATION: Synthetically generated peptide
<221> NAME/KEY: MOD_RES
<222> LOCATION: 1
<223> OTHER INFORMATION: Xaa = Ac-Leu ("Ac" is an acetyl group)
<221> NAME/KEY: MOD_RES
<222> LOCATION: 4
<223> OTHER INFORMATION: Xaa = Leu-epoxide ("epoxide" is an
      alpha-methyl-alpha, beta-epoxide group)

<400> SEQUENCE: 13

Xaa Leu Ala Xaa
 1

<210> SEQ ID NO 14
<211> LENGTH: 4
<212> TYPE: PRT
<213> ORGANISM: Artificial Sequence
<220> FEATURE:
<223> OTHER INFORMATION: Synthetically generated peptide
<221> NAME/KEY: MOD_RES
<222> LOCATION: 1
```

```
<223> OTHER INFORMATION: Xaa = Ac-Leu ("Ac" is an acetyl group)
<221> NAME/KEY: MOD_RES
<222> LOCATION: 4
<223> OTHER INFORMATION: Xaa = Leu-epoxide ("epoxide" is an
      alpha-methyl-alpha, beta-epoxide group)

<400> SEQUENCE: 14

Xaa Leu Phe Xaa
 1

<210> SEQ ID NO 15
<211> LENGTH: 4
<212> TYPE: PRT
<213> ORGANISM: Artificial Sequence
<220> FEATURE:
<223> OTHER INFORMATION: Synthetically generated peptide
<221> NAME/KEY: MOD_RES
<222> LOCATION: 1
<223> OTHER INFORMATION: Xaa = Ac-Leu ("Ac" is an acetyl group)
<221> NAME/KEY: MOD_RES
<222> LOCATION: 4
<223> OTHER INFORMATION: Xaa = Leu-epoxide ("epoxide" is an
      alpha-methyl-alpha, beta-epoxide group)

<400> SEQUENCE: 15

Xaa Ala Leu Xaa
 1

<210> SEQ ID NO 16
<211> LENGTH: 4
<212> TYPE: PRT
<213> ORGANISM: Artificial Sequence
<220> FEATURE:
<223> OTHER INFORMATION: Synthetically generated peptide
<221> NAME/KEY: MOD_RES
<222> LOCATION: 1
<223> OTHER INFORMATION: Xaa = Ac-Leu ("Ac" is an acetyl group)
<221> NAME/KEY: MOD_RES
<222> LOCATION: 4
<223> OTHER INFORMATION: Xaa = Leu-epoxide ("epoxide" is an
      alpha-methyl-alpha, beta-epoxide group)

<400> SEQUENCE: 16

Xaa Phe Leu Xaa
 1

<210> SEQ ID NO 17
<211> LENGTH: 4
<212> TYPE: PRT
<213> ORGANISM: Artificial Sequence
<220> FEATURE:
<223> OTHER INFORMATION: Synthetically generated peptide
<221> NAME/KEY: MOD_RES
<222> LOCATION: 1
<223> OTHER INFORMATION: Xaa = Ac-Ala ("Ac" is an acetyl group)
<221> NAME/KEY: MOD_RES
<222> LOCATION: 4
<223> OTHER INFORMATION: Xaa = Leu-epoxide ("epoxide" is an
      alpha-methyl-alpha, beta-epoxide group)

<400> SEQUENCE: 17

Xaa Leu Leu Xaa
 1

<210> SEQ ID NO 18
<211> LENGTH: 4
<212> TYPE: PRT
<213> ORGANISM: Artificial Sequence
<220> FEATURE:
<223> OTHER INFORMATION: Synthetically generated peptide
<221> NAME/KEY: MOD_RES
```

-continued

```
<222> LOCATION: 1
<223> OTHER INFORMATION: Xaa = Ac-hF ("Ac" is an acetyl group and "hF"
      is homophenylalanine)
<221> NAME/KEY: MOD_RES
<222> LOCATION: 4
<223> OTHER INFORMATION: Xaa = Leu-epoxide ("epoxide" is an
      alpha-methyl-alpha, beta-epoxide group)

<400> SEQUENCE: 18

Xaa Leu Phe Xaa
 1

<210> SEQ ID NO 19
<211> LENGTH: 10
<212> TYPE: PRT
<213> ORGANISM: Homo sapiens

<400> SEQUENCE: 19

Arg Ala Ala Leu Gly Asn Ile Ser Glu Asn
 1               5                  10
```